US006277880B1

(12) United States Patent
Burke et al.

(10) Patent No.: US 6,277,880 B1
(45) Date of Patent: *Aug. 21, 2001

(54) CHEMICAL COMPOUNDS

(75) Inventors: Philip John Burke, London; Robert Ian Dowell, Congleton, both of (GB); Anthony Brian Mauger, Kensington, MD (US); Caroline Joy Springer, London (GB)

(73) Assignees: Zeneca Limited; Cancer Research Campaign Technology Limited, both of London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/314,894

(22) Filed: May 19, 1999

Related U.S. Application Data

(63) Continuation of application No. 08/956,008, filed on Oct. 22, 1997, now Pat. No. 5,958,971, which is a continuation of application No. 08/722,669, filed on Sep. 30, 1996, now Pat. No. 5,714,148, which is a division of application No. 08/361,424, filed on Dec. 21, 1994, now Pat. No. 5,587,161, which is a division of application No. 08/094,952, filed on Jul. 23, 1993, now Pat. No. 5,405,990.

(30) Foreign Application Priority Data

| Jul. 23, 1992 | (GB) | 9215636 |
|---|---|---|
| May 26, 1993 | (GB) | 9310884 |

(51) Int. Cl.$^7$ .................................................. A61K 31/27
(52) U.S. Cl. ........................ 514/479; 514/490; 514/381; 514/558
(58) Field of Search ................................. 514/479, 490, 514/381, 559

(56) References Cited

U.S. PATENT DOCUMENTS

| 4,975,278 | 12/1990 | Senter et al. . |
| 5,405,990 | 4/1995 | Burke et al. . |
| 5,587,161 | 12/1996 | Burke et al. . |
| 5,660,829 | 8/1997 | Burke et al. . |

FOREIGN PATENT DOCUMENTS

| 8910140 | 11/1989 | (WO) . |
| 9002729 | 3/1990 | (WO) . |
| 9103460 | 3/1991 | (WO) . |
| 9308288 | 4/1993 | (WO) . |
| 8807378 | 10/1998 | (WO) . |

OTHER PUBLICATIONS

Edwards/Foster/Owen/Pringle: Cytotoxic Compounds XVII: Perkin J.C.S., 1 (1973): 2397–2402.
Benn/Creighton/Owen/White: Cytotoxic Compounds II (1961): 2365–2375.
Wilman, D. E. V.: Prodrugs in Cancer Chermotherapy: Biochem. Soc. Trans. 14 (1986): 375–382.
Springer, C.J., J. Med. Chem., 33, (1990), 677–681.
Levy C.C., J. Bio. Chem., 212, (1967), 2933–2938.
Pratt, A. G., J. Med. Chem., 243, (1968), 6367–6372.
Levy, C.C., J. Bio Chem., 242, (1967), 2933–2938.
McCullough, J.L., J. Bio Chem., 246, (1971), 7207–7213.
Goldman, P., Proc. N.A.S., 58, (1967), 1299–1306.
Rosowsky, A., Progress in Medicinal Chemistry, 26, (1990), 145–159.
Adamson P.C., J. Clinical Oncology, 10, (1992), 1359–1364.
Bisset, G.M.F., J. Med. Chem., 35, (1992), 859–866.
Sherwood, R.F., Eur. J. Biochem., 148 (1985), 447–453.
Bagshawe K.D., Br. J. Cancer, 58, (1988) 700–703.
Springer C.J., J. Med. Chem., 33 (1990), 677–681.
Antoniw C.J., Br. J. Cancer, 62, (1990), 909–914.
Mann, J., Tetrahedron, 46, (1990), 5377–5382.
Springer, C.J. Eur J. Cancer, 27, (1991), 1361–1366.
Bagshawe, K.D., Disease Markers, 9, (1991), 233–238.
Springer, C. J., Anti–Cancer Drug Design, 6, (1991), 467–479.
Springer, C. J., Drugs of the Future, 18(3), (1993), 212–215.
Bagshawe, K.D., Monoclonal Antibodies and Immunoconjugates, (1990), 95–102.
Springer, C. J., Monoclonal Antibodies—Antibodies in Clinical Oncology, (1991), 185–191.
Bagshawe, K.D. Proc. 4th Intern. Conf. on Monoclonal Antibody Immunoconjugates for Cancer, (1989), 178.
Sharma, S. K., Disease Markers, 9 (1991), 225–231.
Springer, C. J. Proc. Advances in the Applications of Monoclonal Antibodies in Clinical Oncology, RPMS, UK 34, (1989).
Bagshawe, K.D., Biol. Proc. 17th Intern. Soc. Oncodevelopmental Biology & Medicine, Germany (1989).
Melton, R. G., Proc. NATO Adv. Studies Inst., Greece (1984).
Antoniw, P., Proc., 18th Intern. Soc. Oncodevelopment Biology & Medicine, Russia (1990).
Sharma, S. K. Proc. 18th Intern. Soc. Oncodevelopment Biology & Medicine, Russia (1990).
Springer, C. J., Proc. Adv. in Applications of Monoclonal Antibodies in Clinical Oncology RPMS, UK 23 (1990).
Sunters, C. J. Biochem. Pharmacology, 44(1), (1992), 59–64.
Blakey, D. C., Proc. 9th Intern. Hammersmith Meeting, Porto Carras, Greece 33, (1992).
Springer, C. J., Proc. 9th Intern. Hammersmith Meeting, Advances in Applications of Monoclonal Antibodies in Clinical Oncology, Porto Carras, Greece 35 (1992).
Sunters, A., Br. J. Cancer, 60 (1992).

(List continued on next page.)

*Primary Examiner*—Rebecca Cook
(74) *Attorney, Agent, or Firm*—Pillsbury Winthrop LLP

(57) ABSTRACT

Prodrugs, of generic formula I, are disclosed for use in antibody directed enzyme prodrug therapy (ADEPT). The prodrugs are substrates for carboxypeptidase G2 (CPG2) and yield more active cytotoxic drugs than known products of CPG2 catalysed reactions.

15 Claims, No Drawings

OTHER PUBLICATIONS

Blakey, D. C., Br. J. Cancer, 67 (1992).

Sharma, S. K., Proc. Advances in the Applications of Monoclonal Antibodies in Clinical Oncology, London, UK 53 (1989).

Sharma, S. K. Antib. Immunoconj. & Radiopharm. 6 (1993), 74.

Sharma, S. K., Proc. 10th Intern. Hammersmith Meeting—Advances in Applications of Monoclonal Antibodies in Clinical Oncology, Paphos, Cyprus, (1993), 24–25.

Bagshawe, K. D., Antib. Immunoconj. & Radiopharm, (1992), 133.

Springer, C. J., Antib. Immunoconj. & Radiopharm., (1991), 226.

Bagshawe, K. D., Antib. Immunoconj. & Radiopharm, (1991), 204.

Springer, C. J., Antib. Immunoconj. & Radiopharm., (1992), 127.

Bagshawe, K. D., Antib. Immunoconj. & Radiopharm., 4 (1991), 915–922.

Springer, C. J., Proc. 3rd Intern. Conf. on Monoclonal Antibody Immunoconjugates for Cancer, UCSD, USA (1988),43.

Springer, C. J., Antib. Immunoconj. & Radiopharm. 3 (1990), 61.

Bagshawe, K. D., Proc. 4th Int. Conf. on Monoclonal Antibody Immunoconjugates for Cancer, USCD, USA (1989) 178.

Sharma, S K., Antib. Immunoconj. & Radiopharm., 5, (1992) 348.

Springer, C. J., Antib. Immunoconj. & Radiopharm., 6 (1993), 74.

Springer, C. J., Comparasion of Half Lives and Cytotoxicity of Prodrugs & their Activated Drugs in Antibody Directed Enzyme Prodrug Therapy (Adept); Proc. Targeted Cancer Therapy, London, 1991.

Springer, C. J., Proc 10th Int. Hammersmith Meeting—Advances in Application of Monoclonal Antibodies in Clinical Oncology, Cyprus (1993).

Bagshawe, K.D., (1989) Proc. Advances in Applications of Monoclonal Antibodies in clerical Oncology, London,U.K.

Sharma et al., (1990) Antibody directed enzyme prodrug therapy (ADEPT) in human tumour xenograft models, B. J. Cancer, 62: 487.

Parasmickiene, Izv. Akad. Nasuk. SSSR Ser. Khim (3) 649–51 (1971).

G. Parasmickiene et al., 'Sythesis of amino acid derivatives acylated by p–[bis(2–chloropropyl)amino]phenyl alkanoic acids' Chemical Abstracts, vol. 75, No. 5; Aug. 2, 1971, p. 564, bstract No. 36603m.

K. Karpavicius et al., 'N–p–[Bis(2–chloroethyl)amino]phenylacetyl dicarboxylic amino acids and their derivatives' Chemical Abstracts, vol. 75, No. 1; Jul. 5, 1971, p. 526, Abstract No. 6299z.

M. H. Benn et al., 'Cytotoxic Compounds. Part II. Some Amides of the "Nitrogen Mustard" Type.' Journal of the Chemical Society 1961; pp. 2365–2375.

P.D. Edwards et al., 'Cytotoxic compounds Part XVII. o–,m–, and p–Bis(2–chloroethylamino)phenol,p–[N–(2–chloroethyl methylamino]phenol, N,N–bis–2–chloroethyl–p–phenylenediamine, and N,N–bis(2–chloroethyl)–N'–methyl–p–phe nylenediamine as sources of biologically active carbamates'; Journal of the Chemical Society, Perkin Transactions a, No. 20, 1973 p. 2397, –2402.

Karpavicius, Izv. Adad. Nauk. SSSR Ser. Khim (3) 2150–3 (1970).

Bagshawe, K.D., Tumour Site Activation of Cytotoxic Agent; Advances in Applications of Monoclonal Antibodies in Clinical Oncology; Hammersmith Hospital Meeting; 1988.

Bagshawe, K.D., Antibody Directed Enzymes Activate Anti– Cancer Prodrugs, Biochem Soc Trans; 1990.

Canevari et al., Annals of Oncology, vol. 5, pp. 698–701 (1994).

Hermenin et al., Behring Inst. Mitt., No. 82, pp. 197–215 (1988).

CHEMICAL COMPOUNDS

This is a continuation of application Ser. No. 08/956,008, filed Oct. 22, 1997 now U.S. Pat. No. 5,958,971, which is a continuation of Ser. No. 08/722,669 filed Sep. 30, 1996 now U.S. Pat. No. 5,714,148 which is a divisional of U.S. Ser. No. 08/361,424 filed Dec. 21, 1994 now U.S. Pat. No. 5,581,171; which is a divisional of U.S. Ser. No. 08/094,952 filed Jul. 23, 1993 now U.S. Pat. No. 5,405,990.

The invention relates to compounds for use in antibody directed enzyme prodrug therapy (ADEPT), processes for their preparation, pharmaceutical compositions containing them and methods for their use as well as to a two component system comprising 1) a conjugate of an enzyme and an antibody or antibody fragment and 2) a compound of the present invention. The compounds are particularly of interest as pro-drugs for use in conjunction with carboxypeptidase G enzymes, particularly carboxypeptidase G2 (CPG2).

Many cytotoxic compounds have been discovered which are of potential use in cancer chemotherapy. Nitrogen mustards form one important family of such cytotoxic compounds. The clinical use of cytotoxic compounds in general and nitrogen mustards in particular has been limited because of the poor selectivity in the cytotoxic effect between tumour cells and normal cells.

One approach to overcome this problem has involved the development of so-called pro-drugs which are derivatives of the cytotoxic drug, often a relatively simple derivative, whose cytotoxic properties are considerably reduced compared to those of the parent drug. Proposals have been made for the administration of such pro-drugs to patients under regimes whereby the pro-drug is only converted to the cytotoxic drug in the region of the intended site of action.

One approach involves linkage of a cytotoxic parent nitrogen mustard with an amino acid to form a pro-drug which can be converted to the parent nitrogen mustard at the site of intended action under the influence of an enzyme. This approach can be put into practise by the utilisation of an antibody/enzyme conjugate in association with a pro-drug. The antibody/enzyme conjugate is formed from an antibody selective for tumours and an enzyme that will convert the pro-drug to the cytotoxic drug. In clinical practice, the antibody/enzyme conjugate is first administered to the patient and is allowed to bind to the tumour. After a suitable period of time, to allow clearance of the antibody/enzyme conjugate from the rest of the body, the pro-drug is administered to the patient. Conversion of the pro-drug, under the influence of the localised enzyme, to the cytotoxic drug takes place mainly in the region of the tumour. Such a system is described in International Application PCT/GB88/00181 published as WO88/07378 and U.S. Pat. No. 4,975,278.

Known pro-drugs for ADEPT cleaved by CPG yield benzoic acid mustards as their active drugs. However there is a need for more active drugs to be produced by CPG cleavage to increase the therapeutic potency against tumour cells. A further need arises to increase the selectivity of ADEPT therapy with CPG, that is to say the ratio of toxicity to cancer cells compared with healthy cells.

The present invention is based on the discovery of novel pro-drugs for use in ADEPT therapy that are cleaved by CPG and which yield significantly more active cytotoxic drugs than known products of CPG catalysed reactions. CPG acts naturally as a folate degrading enzyme which specifically hydrolyses glutamic and aspartic acids from folate derivatives (Sherwood, R. F. et al., Eur. J. Biochem. (1985), 148, 447–453). Carboxypeptidase G enzymes do not recognise non-classical folate analogues (Kalghatgi, K. K. et al., Cancer Research (1979), 39, 3441–3445) and are therefore considered conservative in substrate specificity. Surprisingly the pro-drugs of the present invention are substrates for CPG enzymes such as CPG1, but particularly for CPG2 enzymes. CPG2 is an exopeptidase with specificity for L-glutamate. It is known to hydrolyse the glutamic acid moiety from folic acid and analogues thereof and glutamyl-p-aminobenzoic acid by cleavage at —CO—NH— of the partial structure -aromatic ring-CO—NH-Glu. In the present invention a partial structure for comparative purposes is -aromatic-ring-X—CO—NH-Glu wherein X is —NH—, —O— or —CH2—; thus altering the distance between the cleavage point and the aromatic ring as well as altering the electron distribution across the —CO—NH— bond, particularly when X is NH or O. CPG2 could not be predicted to accommodate these spatial and electronic differences.

According to one feature of the present invention there are provided compounds of Formula I, which are pro-drug substrates for CPG enzymes, Formula I

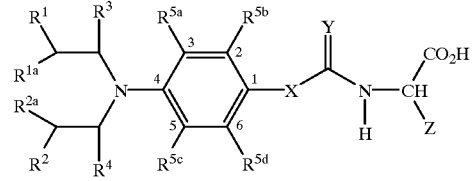

wherein $R^1$ and $R^2$ each independently represents chlorine, bromine, iodine, $OSO_2Me$, or $OSO_2phenyl$ (wherein phenyl is optionally substituted with 1,2,3,4 or 5 substituents independently selected from $C_{1-4}$alkyl, halogen, —CN or —$NO_2$);

$R^{1a}$ and $R^{2a}$ each independently represents hydrogen, $C_{1-4}$alkyl or $C_{1-4}$haloalkyl;

$R^3$ and $R^4$ each independently represents hydrogen, $C_{1-4}$ alkyl or $C_{1-4}$ haloalkyl;

R5a, R5b, R5c and R5d each independently represents hydrogen, $C_{1-4}$ alkyl optionally containing one double bond or one triple bond, $C_{1-4}$ alkoxy, halogen, cyano, —$NH_2$, —$CONR^7R^8$ (wherein $R^7$ and $R^8$ are as defined below), —$NH(C_{1-4}$-alkyl), —$N(C_{1-4}$-alkyl$)_2$ and $C_{2-5}$alkanoyl; or R5a and R5b together represent
  a) C4 alkylene optionally having one double bond;
  b) C3 alkylene; or
  c) —CH=CH—CH=CH—, —CH=CH—CH2— or —CH2—CH=CH— each optionally substituted with 1, 2, 3 or 4 substituents said substituents each independently selected from the group consisting of $C_{1-4}$ alkyl, $C_{1-4}$ alkoxy, halogen, cyano, nitro, $C_{2-5}$alkanoyl and —CONR7R8 (wherein R7 and R8 are as defined below);

X represents O, NH or —$CH_2$—;

Y represents O;

Z represents —V—W where V is —CH2—T— in which T is —CH2—, —O—, —S—, —(SO)— or —($SO_2$)— (provided that when V has sulphur or oxygen as its second atom, W is other than —COOH) and said group V optionally further carrying one or two substituents Q1 and/or Q2 on carbon;

wherein $Q^1$ and $Q^2$ each independently represents $C_{1-4}$ alkyl or halogen; or, when Q1 and Q2 are bonded to adjacent carbon atoms, $Q^1$ and $Q^2$ together may additionally represent a $C_3$–$C_4$alkylene radical optionally substituted with 1, 2, 3 or 4 substituents independently selected from the group consisting of $C_{1-4}$alkyl and halogen; and W represents
(1) COOH,
(2) —(C=O)—O—R6 wherein R6 represents a $C_{1-6}$alkyl, $C_{3-6}$cycloalkyl or aryl (as defined in 3 below) group;
(3) —(C=O)—NR7R8 wherein R7 and R8 each independently represent hydrogen or a C1–6alkyl, C3–6cycloalkyl, aryl, heteroaryl linked to N via carbon or C7–9aralkyl group wherein aryl is phenyl; heteroaryl is a 5 or 6 membered ring containing 1 to 3 heteroatoms selected from the group consisting of nitrogen and sulphur; the aryl moiety per se, the heteroaryl moiety and the aryl moiety of the aralkyl group may be substituted on carbon with 1–4 substituents selected from the group consisting of —COOH, —OH, —NH$_2$, —CH$_2$—NH$_2$, —(CH2)$_{1-4}$-COOH, tetrazol-5-yl and —SO$_3$H and the alkyl moiety may optionally carry a methyl group;
(4) —SO$_2$NHR9 wherein R9 is as defined for R7 but may additionally represent —CF$_3$, —CH$_2$CF$_3$ or aryl as defined above;
(5) SO$_3$R10 in which R10 represents H, $C_{1-6}$alkyl or $C_{3-6}$cycloalkyl,
(6) PO$_3$R10R10 (wherein the R10 radicals, which may be the same or different, are as herein defined)
(7) a tetrazol-5-yl group;
(8) —CONH—SO$_2$R11 in which R11 represents
  (a) $C_{3-7}$cycloalkyl;
  (b) $C_{1-6}$-alkyl optionally substituted with substituents selected from the group consisting of aryl as defined below, $C_{1-4}$-alkyl, CF$_3$ or halogen; and
  (c) perfluoro-$C_{1-6}$alkyl; wherein aryl is phenyl or phenyl having 1–5 substituents wherein the substituents are selected from the group consisting of halogen, —NO$_2$, —CF$_3$, $C_{1-4}$alkyl, $C_{1-4}$alkoxy, —NH$_2$, —NHCOCH$_3$, —CONH$_2$, —OCH$_2$COOH, —NH($C_{1-4}$-alkyl), —N($C_{1-4}$-alkyl)$_2$, —NHCOOC$_{1-4}$alkyl, —OH, —COOH, —CN and —COOC$_{1-4}$alkyl; and
(9)-H-Het wherein H represents S, SO or SO2 and Het represents a 5 or 6 membered heterocyclic aromatic ring linked to M via a carbon atom of the aromatic ring, said aromatic ring containing 1, 2, 3 or 4 heteroatoms selected from the group consisting of O, N and S said aromatic ring optionally being substituted on carbon atoms of the ring with 1, 2, 3 or 4 substituents selected from the group consisting of —OH, —SH, —CN, —CF3, NH2 and halogen; and salts of said compound of formula I.

The compounds of formula I possess at least one asymmetric carbon atom, that being the carbon atom carrying the substituent —COOH in formula I. Moreover, depending on the meanings of $R^1$, $R^2$, $R^3$, $R^4$, $Q^1$ and $Q^2$, the compounds of formula I may carry additional asymmetric carbon atoms. It will be understood that the present invention encompasses all such forms of the compound of formula I, including the racemic form as well as the individual optical isomers thereof which possess the useful physiological properties of the compositions of the present invention defined herein, it being common general knowledge to those skilled in the art how such isomers may be separated and how their physiological properties may be determined. Compounds of the present invention preferably possess an L configuration at the carbon atom carrying the substituent —COOH in Formula I.

The present invention encompasses the salts of the compounds of formula I. It will be appreciated, however, that for pharmaceutical use, the salts referred to will be pharmaceutically acceptable, but other salts may find use, for example in the preparation of compounds of formula I and their pharmaceutically acceptable salts. Polymorphic forms of compounds of the present invention may be prepared and these forms are also encompassed by the invention.

Where any substituent referred to herein represents or contains an alkyl group, such group may be straight chain or branched. Where any substituent referred to herein represents or contains a $C_{1-6}$ alkyl group such group advantageously has 1 to 4 carbon atoms, for example methyl, ethyl, n-propyl or isopropyl, preferably methyl and ethyl, but especially methyl. Where any substituent referred to herein represents or contains a $C_{1-4}$ alkyl group such group may for example be methyl, ethyl, n-propyl or isopropyl, preferably methyl and ethyl, but especially methyl.

Preferred values for $R^1$ and $R^2$ are I, Br, Cl, OSO2Me and OSO$_2$phenyl wherein phenyl is substituted with 1 or 2 (especially 1) substituents (as herein defined) in the 2 and/or 4 positions. Especially preferred values for $R^1$ and $R^2$ are I, Br, Cl and —OSO$_2$Me. A preferred value for $R^{1a}$ and $R^{2a}$ is —CH3 or hydrogen, but especially hydrogen.

Preferred values for $R^3$ and $R^4$ are hydrogen, methyl and CF$_3$, but especially hydrogen.

Preferred values for R5a–d are hydrogen, fluorine, chlorine, methyl, —CONH$_2$ and CN. Where substitution is present on the phenyl ring such that at least one of $R^{5a}$, $R^{5b}$, $R^{5c}$ and $R^{5d}$ is other than hydrogen it is preferred that only one or two of $R^{5a}$, $R_{5b}$, $R^{5c}$ and $R^{5d}$ are other than hydrogen. In such circumstances it is further preferred that $R^{5b}$ and $R^{5d}$ are hydrogen and that $R^{5a}$ and/or $R^{5c}$ is other than hydrogen. It is especially preferred however that $R^{5a-b}$ are hydrogen.

Preferred values for X are O or NH, especially O. In another embodiment of the invention an especially preferred value for X is NH.

A preferred value for V is —CH2—CH2—. In another embodiment of the invention a preferred value for V, when W is tetrazol-5-yl, is —CH2—S—.

Where W represents a group of definition 3, aryl is preferably substituted phenyl and heteroaryl is advantageously a 5 or 6 membered ring containing 1 or 2 heteroatoms, such heteroatoms preferably being nitrogen such as pyridyl or pyrimidinyl. Preferred substituents on the aryl moiety per se, the heteroaryl moiety or the aryl moiety of the aralkyl group are —COOH, —CH$_2$—COOH or tetrazol-5-yl.

Where W represents a group of definition 8(b) in which W represents a C1-6 alkyl group optionally substituted by aryl, the optionally substituted aryl group is preferably phenyl substituted by —CONH$_2$, —OCH$_2$—COOH and/or —COOH, but is especially unsubstituted phenyl.

Where V represents a group of definition 9, Het advantageously represents a 5- or 6-membered heterocyclic aromatic ring containing 1, 2, 3 or 4 nitrogen atoms. Preferably nitrogen is the only heteroatom present in the ring. Particular groups thus include pyridyl, pyrrolyl, 1,2,3-triazinyl and 1,2,4-triazinyl.

Particular values for W are the definitions 1, 2, 3, 5, 6, 7 and 9, preferred definitions being 1, 2, 3, 7 and 9 as detailed hereinbefore.

More particular values for V are
—COOH,
—CONH$_2$,
—CONHR8 (wherein R8 is as. hereinbefore defined, especially wherein R8 is phenyl),
tetrazol-5-yl,
—CONH—SO$_2$R$^{11}$ (wherein R$^{11}$ represents definitions (b) and (c) as detailed hereinbefore) and the group
—M-Het (in which H is S and Het represents a 5-membered heterocyclic aromatic ring with 3 or 4 heteroatoms optionally substituted on carbon where the heterocyclic ring has 3-heteroatoms by a halogen atom or cyano group).

Where W represents —CONH—SO$_2$R$^{11}$ in which R$^{11}$ represents a perfluoro-C$_{1-6}$alkyl group the perfluoroalkyl group preferably has 1 to 4 carbon atoms, especially 1 or 2 carbon atoms.

More particular values for W are —COOH, tetrazol-5-yl or —CONH(aryl) (in which aryl is defined in definition 3 above). In this context, aryl is preferably substituted phenyl, preferred substituents being —COOH, —CH$_2$—COOH or tetrazol-5-yl.

Preferred specific compounds of the invention, by virtue of their utility in ADEPT include:

(S)-2-(4-[bis(2-chloroethyl)amino] phenoxycarbonylamino)-4-(1H-1,2,3,4-tetrazol-5-yl) butyric acid and salts thereof;

N-(4-[bis(2-chloroethyl)amino]-3-fluorophenylcarbamoyl)-L-glutamic acid and salts thereof;

N-(4-[bis(2-chloroethyl)amino]phenylcarbamoyl)-L-glutamic acid and salts thereof;

but an especially preferred compound of the invention is N-(4-[bis(2-chloroethyl)amino]phenoxycarbonyl)-L-glutamic acid and salts thereof.

Another preferred compound, which has shown good activity in tests, is N-(4-[bis(2-iodoethyl)amino] phenoxycarbonyl)-L-glutamic acid and salts thereof.

Particular sub-groups of the compounds of the present invention of interest may be obtained by taking any one of the above mentioned particular or generic definitions for R$^1$–R$^4$, R$^{5a-d}$, X, Y, W, Q1 or Q2 either singly or in combination with any other particular or generic definition for R$^1$–R$^4$, R$^{5a-d}$, X, Y, W, Q1 or Q2.

Furthermore drugs produced by CPG cleavage of tested compounds of the present invention for effective ADEPT are less stable under physiological conditions than known drug products of CPG2 catalysed reactions. This reduced stability produces less toxicity to healthy cells, than if the drugs had stabilities similar to known products of CPG catalysed reactions for ADEPT, if a proportion of active drug produced at the tumour site leaks into the general circulation. Thus tests we have conducted demonstrate that even after intravenous administration of drug (that is active drug, not pro-drug), 15 min later, the drug was not detectable in plasma.

The compounds of this invention form salts with various inorganic and organic acids and bases and such salts are within the scope of the invention. Such salts include ammonium salts, alkali metal salts like sodium and potassium salts, alkaline earth metal salts like the calcium and magnesium salts, salts with organic bases; e.g. dicyclohexylamine salts, N-methyl-D-glucamine, salts with amino acids like arginine, lysine, and the like. Also, salts with organic and inorganic acids may be prepared; e.g., HCl, HBr, H$_2$SO$_4$, H$_3$PO$_4$, methanesulfonic, toluenesulfonic, and camphorsulfonic. Preferably the acids are strong acids having pK$_a$ values less than or equal to 2 and especially having pKa values less than or equal to 1. Physiologically acceptable salts are preferred, although other salts may be useful; e.g., in isolating or purifying the product.

The salts can be formed by conventional means such as by reacting the free acid or free base forms of the product virth one or more equivalents of the appropriate base or acid in a solvent or medium in vhich the salt is insoluble, or in a solvent such as water which is then removed in vacuo or by freeze-drying or by exchanging the cations of an existing salt for anocher cation on a suitable ion exchange resin.

According to a further feature of the present invention there is provided a process for the preparation of compounds of formula I and salts thereof which comprises deprotecting a compound of the formula:

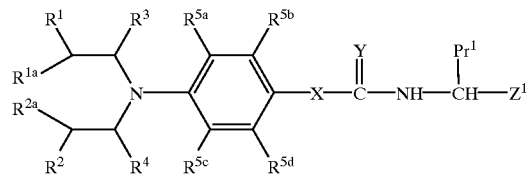

Ia (wherein R$^1$, R2, R$^{1a}$, R$^{2a}$, R$^3$, R$^4$, R$^{5a}$, R$^{5b}$, R$^{5c}$, R$^{5d}$, X, Y Q$^1$ and Q$^2$ are as hereinbefore defined and Z$^1$ represents Z as hereinbefore defined vith the proviso that when W is a carboxyl group it is present in protected form (denoted Pr$^2$) and Pr$^1$ also represents a carboxyl group in protected form (which may be the same or different to Pr$^2$) and if desired converting a compound of formula I thus obtained into a salt thereof.

Pr$^1$ and Pr$^2$ may thus for example represent benzyloxycarbonyl groups, t-butyloxy carbonyl groups, 2-(trimethylsilyl)ethyl ester, dimethyl-tert-butylsilyl ester, diphenylmethyl ester, tetrahydropyran ester, tetrahydroturan ester, methoxyethoxymethyl ester or benzyloxymethyl ester or other generally known carboxy protecting groups, for example ester forming protecting groups, for deprotection by hydrogenolysis or acid catalysis (Greene, T. W. and Wuts, P. G. H. in Protective Groups in Organic Synthesis, 2nd Edition, Wiley-Interscience, 1990).

Where Pr$^1$ and/or Pr$^2$ represents a benzyloxycarbonyl group, deprotection is preferably effected by hydrogenation. Such hydrogenation may be effected by any convenient means such as in the presence of platinum or Raney nickel, but is preferably effected by the use of palladium in the presence of carbon. The hydrogenation is advantageously effected in the presence of an inert solvent, preferably a non-protonic solvent, especially ethyl acetate, tetrahydrofuran or polar aprotic solvent such as dimethylformamide; preferably at a temperature of 0–100° C., more preferably at a temperature of 15–50° C. and especially at ambient temperature; and preferably for 1–24 h.

Where Pr$^1$ and/or Pr$^2$ represents a t-butyloxycarbonyl group, the deprotection reaction may advantageously be effected in the presence of an acid, advantageously a strong acid such as trifluoroacetic acid HCl, HBr, HI or formic acid. Where it is desired to use a solvent, inert non protonic solvents such as CH$_2$Cl$_2$ or diethyl ether are preferred. The reaction is conveniently effected at a temperature of 0–100° C., more conveniently at 0–30° C. and especially at ambient temperature.

The compounds of formula Ia (as hereinbefore defined) and the salts thereof are novel and thus constitute a further feature of the present invention.

According to a further feature of the present invention there is provided a process for the preparation of compounds of formula Ia, wherein X is O and Y is O, and the salts thereof which process comprises reacting a compound of the formula:

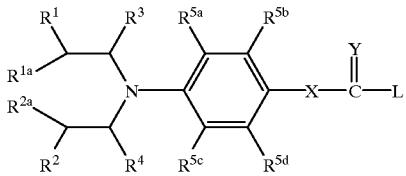

(II)

(wherein $R^1$, $R^2$, $R^{1a}$, $R^{2a}$, $R^3$, $R^4$, $R^{5a}$, $R^{5b}$, $R^{5c}$ and $R^{5d}$ are as hereinbefore defined X is O, Y is O and L represents a leaving atom or group) with a compound of the formula:

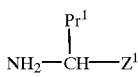

(III)

(wherein $Pr^1$ and $Z^1$ are as hereinbefore defined) whereby to form a compound of formula Ia, and, if desired, converting the compound of formula Ia to a salt thereof. Advantageously L is Cl, Br, I, 4-nitrophenoxy or pentafluorophenoxy. Conveniently the reaction is effected in the presence of a solvent at a temperature of −10° C. to 100° C. and preferably at 20–50° C.

Preferred reaction conditions include effecting the reaction in the presence of an organic solvent (especially chloroform, ethyl acetate, toluene, dimethylformamide and $CH_2Cl_2$) preferably at 5–50° C. preferably for 1–24 h. Compounds of formula (II) constitute a further feature of the present invention which compounds may for example be prepared by reacting a corresponding phenol containing an anilino mustard group either with an aryl chloroformate, for example nitrophenyl chloroformate (especially 4-nitrophenylchloroformate) or with phosgene whereby to form a compound of formula (II).

Preferred reaction conditions include effecting the reaction in the presence of an organic solvent (especially ethyl acetate or chloroform), preferably at 15–50° C. (especially at ambient temperature), preferably for 1–10 h.

Compounds of formula (III) wherein W represents group (3) as herein defined may be prepared from compounds of formula (III) wherein W represents group (2) as herein defined using standard conditions. Preferable standard conditions include reaction with nitrogen nucleophiles (especially ammonia or a primary or secondary amine) preferably at 25–50° C. preferably for about 24 h.

Compounds of formula (III) wherein W represents a tetrazol-5-yl group may be prepared from the corresponding nitrile by known methods for example that described by Finnegan, W G et al., JACS, 80, 1978, 3909 followed by deprotection of the amine ($Pr^3$) whereby to form compounds of formula (III) wherein W is tetrazol-5-yl.

Compounds of formula (III) wherein W represents group (9) as herein defined may be prepared by reduction of compounds of formula (XV) as herein defined to a corresponding primary alcohol using standard conditions (especially using diborane, or a mixed anhydride reaction followed by sodium borohydride reduction). The corresponding primary alcohol is converted by standard methods for example using methane sulphonyl chloride and trimethylamine at 0° C. in the presence of $CH_2Cl_2$ into a leaving group such as Br, I or mesylate; which leaving group is displaced by a group of formula:

HS-Het   (XVI)

(wherein Het is as hereinbefore defined for W=(9)) whereby, after treatment under oxidising conditions, to form compounds of formula:

XVII

(wherein $Z^{111}$ represents Z as hereinbefore defined with the proviso that W represents —S-Het, —(S=O)-Het or —$SO_2$-Het, and $Pr^1$ and $Pr^3$ are protected carboxyl and —$NH_2$ groups respectively as hereinbefore defined). Suitable oxidising conditions include treatment with an oxidising agent (especially 3-chloroperbenzoic acid). Deprotection of the —$NH_2$ group of compounds of formula (XVII) under standard conditions as hereinbefore defined is effective to form a compound of formula (III) wherein W represents group (9) as hereinbefore defined.

According to a further feature of the present invention there is provided a process for the preparation of compounds of formula Ia, wherein X is N and Y is O, and the salts thereof, which process comprises reacting a compound of the formula:

(IV)

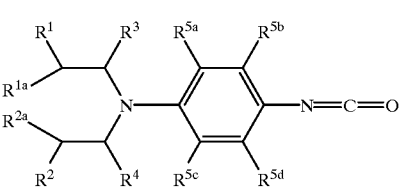

(wherein $R^1$, $R^2$, $R^{1a}$, $R^{2a}$, $R^3$, $R^4$ and $R^{5a-d}$ are as hereinbefore defined) or a salt thereof with a compound of the formula (III) as hereinbefore defined whereby to form a compound of formula Ia, and, if desired, converting the compound of formula Ia to a salt thereof. The reaction may for example be effected in the presence of an organic solvent (preferably polar aprotic, especially $CH_2Cl_2$ or ethyl acetate) preferably at room temperature preferably for about 1–5 hour.

According to a further feature of the present invention there is provided a process for the preparation of compounds of formula (IV) and the salts thereof, which process comprises reacting a compound of formula (V) (wherein $R^1$, $R^2$, $R^{1a}$, $R^2a$, $R^3$, $R^4$, and $R^{5a-d}$ are as hereinbefore defined) with a compound of formula $L^1$—(C=O)—$L^2$ (wherein $L^1$ and $L^2$ represent leaving groups) whereby to form a compound of formula (IV). Values for $L^1$ and $L^2$ include Cl, $CCl_3$, imidazolyl and aryloxy (especially phenoxy). Preferred reaction conditions include effecting the reaction in the presence of an organic solvent (preferably polar aprotic, especially ethyl acetate) at 5–25° C. for about 15 min.

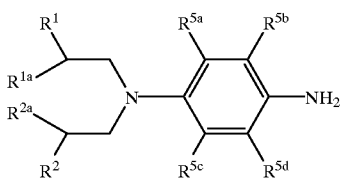

(V)

According to a further feature of the present invention there is provided a process for the preparation of compounds of formula (Ia) as hereinbefore defined, wherein X is —CH$_2$— and Y is O, and the salts thereof which process comprises: reacting a compound of formula (II) or a salt thereof, as hereinbefore defined, with the provisos that X is —CH$_2$—, Y is O and L is advantageously pentafluorophenoxy, Cl, —O—(CO)-C$_{1-6}$alkyl preferably branched alkyl, especially C$_{1-4}$alkyl and the product of a corresponding phenyl acetic acid containing an anilino mustard reacted with a carbodiimide (especially dicyclohexylcarbodiimide); with a compound of formula (III) as hereinbefore defined using standard reaction conditions (for example effecting the reaction in the presence of polar aprotic solvents such as dimethylformamide, ethyl acetate or tetrahydrofuran for 1–24 h at 20–50° C.) whereby to form a compound of formula (Ia), and, if desired, converting the compound of formula (Ia) to a salt thereof. Compounds of formula (II) may be prepared using standard methods from corresponding phenyl acetic acids containing an anilino mustard group.

According to a further aspect of the present invention there is provided a process for the preparation of a compound of formula (Ia) as hereinbefore defined, wherein W represents group (8) (that is —CONH—SO$_2$R$^{11}$) as hereinbefore defined or a salt thereof which process comprises: reacting a compound of formula (III) as hereinbefore defined with the proviso that V only represents group (8); with a compound of formula (II) as hereinbefore defined using reaction conditions known per se whereby to form a compound of formula (Ia) wherein W represents group (8), and, if desired, converting the compound of formula (Ia) into a salt thereof. Preferred reaction conditions include effecting the reaction in the presence of an organic solvent (preferably a polar aprotic solvent, especially ethyl acetate or dichloromethane), preferably at 5–50° C. (especially ambient temperature), preferably for 1–5 h.

Compounds of formula (III) constitute a further aspect of the present invention and such compounds may be prepared by deprotection of the amine group of a compound of formula:

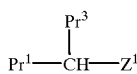

(XI)

(in which Pr$^1$ represents a carboxyl group in protected form as hereinbefore defined, Pr$^3$ represents a —NH$_2$ group in protected form, especially a benzyloxycarbonyl derivative or a phthalimido derivative and Z$^1$ represents Z as hereinbefore defined with the proviso that W represents group (8) under reaction conditions known per se whereby to form a compound of formula (III) wherein v represents group (8) and, if desired, converting the compound of formula (III) into a salt thereof. Preferred reaction conditions include hydrogenation in the presence of palladium on carbon in an organic solvent (preferably polar aprotic, especially ethyl acetate or tetrahydrofuran), preferably at ambient temperature, preferably for 1–24 h. Further preferred reaction conditions include effecting deprotection in the presence of HBr in acetic acid, preferably at ambient temperature, preferably for 1–24 h.

Compounds of formula (XI) may be prepared by reacting a compound of formula:

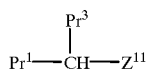

(XV)

(wherein Pr$^1$ and Pr$^3$ are as hereinbefore defined and Z$^{11}$ represents Z as hereinbefore defined with the proviso that W represents only COOH); with a compound of formula R$^{11}$SO$_2$NH$_2$ in which R$^{11}$ is as defined in W=(8) whereby to form a compound of formula (XI) under standard reaction conditions. Standard reaction conditions include carrying out the reaction in an inert solvent (especially dichloromethane) in the presence of a carbodiimide (especially dicyclohexylcarbodiimide) and a base (especially 4-(N,N-dimethylamino)piperidine).

According to a further aspect of the present invention there is provided a process for the preparation of compounds of formula (I) wherein W represents the following groups as hereinbefore defined: (4) (that is —SO$_2$NHR$^9$), (5) (that is —SO$_3$R$^{10}$) and (6) (that is —PO$_3$R$^{10}$R$^{10}$) which process comprises: reacting a compound of formula:

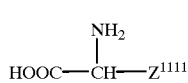

(XVIII)

(wherein Z$^{111}$ represents Z as hereinbefore defined with the proviso that W represents the following groups as hereinbefore defined: (4) (that is —SO$^2$NHR$^9$), (5) (that is —SO$_3$R$^{10}$) and (6) (that is —PO$_3$R$^{10}$R$^{10}$)); with compounds of formula (II) as hereinbefore defined under standard conditions; or with compounds of formula (V) as hereinbefore defined under standard conditions; whereby to form a compound of formula I wherein W represents groups (4), (5) and (6), and, if desired, converting the compound of formula I to a salt thereof. Standard conditions include effecting the reaction with a base (especially triethylamine) in the presence of an organic solvent (preferably aprotic polar, especially dichloromethane), preferably at ambient temperature. Compounds of formula (XVIII) are known (available from Sigma Chemical Co.) or may be prepared from known compounds by standard methods.

According to a further feature of the present invention there is provided a process for the preparation of compounds of formula (Ia) hereinbefore defined, wherein X is N or O, Y is O, R$^1$ and R$^2$ are Cl, Br, I or OSO$_2$Me (especially Cl), R$^{1a}$ is H, R$^{2a}$ is H, R$^3$ is H and R$^4$ is H, and the salts thereof which process comprises reacting a compound of formula:

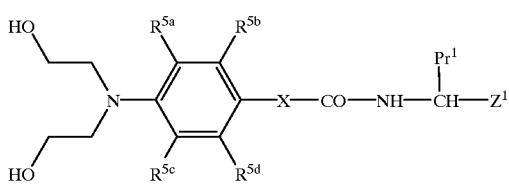

(XIX)

(wherein $R^{5a-d}$, $Pr^1$ and $Z^1$ are as hereinbefore defined and X is O or NH) with either:

a phosphorus halogenating agent (especially phosphorus pentachloride) or thionyl chloride in the presence of an organic solvent (preferably non-polar aprotic, especially $CH_2Cl_2$), preferably heated at reflux for 1–2 h (especially 90 min); or methyl sulphonyl chloride in the presence of an organic solvent (preferably polar aprotic, especially pyridine) whereby to form a compound of Formula (Ia) wherein X is O or NH, Y is O, $R^1$ and $R^2$ are Br, I, $OSO_2Me$ or Cl, $R^{1a}$ is H, $R^{2a}$ is H, $R^3$ is H and $R^4$ is H, and, if desired converting the compounds of formula (Ia) into a salt thereof. When methyl sulphonyl chloride is used, hydroxy groups in the compound of formula (XIX) may be converted into either Cl and/or $OSO_2He$ depending on the temperature used for the reaction. The dichloro compounds (that is $R^1=R^2=Cl$) may conveniently be obtained by effecting the reaction at 70° C. for 15 min; and the corresponding compound where $R^1=Cl$ and $R^2=OSO_2Me$ may conveniently be obtained by effecting the reaction at 50° C. for 10 min.

When $R^1$ and $R^2$ are Br and $R^1$ and $R^2$ are I, methane sulphonyl anhydride is preferably substituted for methane sulphonyl chloride because this removes any problems of competing halogen in the reaction. The compound of formula XIX (0.002M) was dissolved in $CHCl_3$ (30 ml). Triethylamine (1.12 ml) and methysulphonyl anhydride (0.008M) were added at ambient temperature, the mixture stirred for 2 hours and then washed with water. The product so obtained was dried over $MgSO_4$, filtered and evaporated to an oil. The oil was dissolved in dry DMF and lithium iodide (or bromide; 0.005M) added, stirred at 80° C. for 2 hours, cooled, poured into water and extracted with ether. The product so obtained was dried over $MgSO_4$, filtered, evaporated to dryness and purified by flash column chromatography.

Compounds of formula (XIX) may be prepared by reacting a compound of formula:

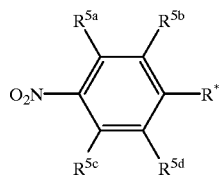

(XX)

(wherein $R^{5a-d}$ are as hereinbefore defined and R respresents —N=C=O or —O—CO—L wherein L represents a leaving group as hereinbefore defined) with a compound of formula (III) as hereinbefore defined to obtain a compound of formula:

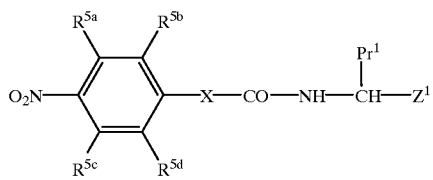

(XXI)

(wherein $R^{5a-d}$; $Pr^1$ and $Z^1$ are as hereinbefore defined and X is O or NH). The compound so obtained is hydrogenated (preferably in the presence of palladium on carbon) to obtain a compound corresponding to formula (XXI) but with $-NH_2$ in lieu of $-NO_2$. The compound so obtained is reacted with ethylene oxide under acid aqueous conditions (prefrably acetic acid/water, 1:1), preferably for 1–2 days, preferably at ambient temperature, whereby to form a compound of formula (XIX). An example of the process is shown in Scheme 5.

A process for the preparation of compounds of formula (I), wherein V represents a tetrazol-5-yl group, comprises reacting a compound of formula:

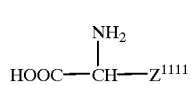

(XVIII)

(wherein $Z^{111}$ represents Z as hereinbefore defined with the proviso that W represents a tetrazol-5-yl group; with compounds of formula (II) as hereinbefore defined under standard conditions; whereby to form a compound of formula I wherein W represents a tetrazol-5-yl group and, if desired, converting the compound of formula I to a salt thereof. The standard conditions include reaction in a polar aprotic solvent (especially DHF) in the presence of a base (preferably dimethylamino pyridine, especially triethylamine) for at least 2 h (preferably 20 h) at a temperature of 20–50° C. (especially 25° C.).

In vitro cytotoxic potency of prodrugs and drugs.

The in vitro cytotoxic potency of prodrugs, prodrugs plus enzyme and drugs was measured in a cytotoxicity assay similar to that described by Skehan et al (J. Natl. Cancer Inst 82, 1107–1112, 1990). LoVo cells (ECACC No: 87060101) were diluted in DMEM media (containing 10% FCS, 1% glutamine and 0.2% gentamycin) plated out in 96 well microtitre plates at a density of 2,500 cells/well and incubated overnight at 37° C. in 5% $CO_2$. Various concentrations of prodrug, corresponding drug as control or prodrug plus enzyme (1U CPG2 activity/well—one unit of enzyme being the amount required to hydrolyse 1 μmole of methotrexate/min/ml at 37°) were added to these cells and following either a 1 hr or 24 hr incubation period the cells were washed, fresh medium added and the cells incubated at 37° C. in 5% $CO_2$. Three days after addition of compound, TCA was added to the wells (16% final concentration) and the amount of cellular protein adhering to the plates was assessed by the addition of SRB dye (Skehan et al). The optical density at 540 nm was measured and expressed as a percentage of the OD540 in control wells which received no compound. The potency was expressed as the concentration required to inhibit cell growth by 50% ($IC_{50}$). Prodrug on its own should generally possess low activity in the test relative to prodrug in the presence of CPG2 (that is CPG2 enzyme is necessary for activation of prodrug to drug). Direct addition of chemically synthesised drug (not needing CPG2 activation) acts as a control in the assay.

Using the methodology described above, representative compounds tested of the invention were evaluated and were found to exhibit a ratio of at least 10 fold greater activity in the presence of CPG2 compared with activity in the absence of CPG2 after 1 h; thereby demonstrating and confirming the utility of the compounds of the invention as effective.

According to a further aspect of the present invention we provide pharmaceutical compositions comprising as pro-drug ingredient at least one compound of Formula I or a physiologically acceptable salt of said compound in association with a pharmaceutically acceptable carrier or diluent. The composition will conveniently comprise an effective amount of the pro-drug to be used with a CPG (preferably CPG2)-tumour selective antibody conjugate already localised at the tumour.

According to a further aspect of the present invention we provide sterile pharmaceutical compositions for injection comprising as pro-drug ingredient at least one compound of Formula I or a physiologically acceptable salt of said compound in association with a pharmaceutically acceptable carrier or diluent. The composition will conveniently comprise an effective amount of the pro-drug.

According to a further aspect of the present invention we provide a two component system, each component for use in association with the other, which comprises:

i) a first component that is an antibody or fragment thereof capable of binding a given antigen, the antibody or fragment thereof being conjugated to a CPG (preferably carboxypeptidase G2) enzyme capable of converting a compound of formula I or physiologically acceptable salt thereof into a cytotoxic drug; and ii) a second component that is a compound of formula I or a physiologically acceptable salt thereof convertible under the influence of the CPG (preferably carboxypeptidase G2) enzyme to the cytotoxic drug.

The antibody or fragment thereof is preferably capable of binding with a tumour associated antigen.

A particular antibody capable of binding with a tumour associated antigen is mouse monoclonal antibody A5B7. Antibody A5B7 binds to human carcinoembryonic antigen (CEA) and is particularly suitable for targeting colorectal carcinoma. A5B7 is available from DAKO Ltd., 16 Manor Courtyard, Hughenden Avenue, High Wycombe, Bucks HP13 5RE, England, United Kingdom. Antibody fragments can be prepared from whole IgG antibody by conventional means such as for example F(ab')$_2$ fragments as described by Mariani, M. et al (1991), Molecular Immunology 28, 69–77. In general the antibody (or antibody fragment)—enzyme conjugate should be at least divalent, that is to say capable of binding to at least 2 tumour associated antigens (which may be the same or different). Antibody molecules may be humanised by known methods such as for example by "CDR grafting" as disclosed in EP239400 or by grafting complete variable regions onto human constant regions as disclosed in U.S. Pat. No. 4,816,567. Humanised antibodies may be useful for reducing immunogenicity of an antibody (or antibody fragment). A humanised version of antibody A5B7 has been disclosed in PCT WO92/01059.

The hybridoma which produces monoclonal antibody A5B7 was deposited with the European Collection of Animal Cell Cultures, Division of Biologics, PHLS Centre for Applied Microbiology and Research, Porton Down, Salisbury, Wiltshire SP4 0JG, United Kingdom. The date of deposit was Jul. 14th 1993 and the accession number is No. 93071411. Antibody A5B7 may be obtained from the deposited hybridoma using standard techniques known in the art such as documented in Fenge C, Fraune E & Schuegerl K in "Production of Biologicals from Animal Cells in Culture" (Spier R E, Griffiths J R & Heignier B, eds) Butterworth-Heinemann, 1991, 262–265 and Anderson B L & Gruenberg M L in "Commercial Production of Monoclonal Antibodies" (Seaver S, ed), Marcel Dekker, 1987, 175–195. The cells may require re-cloning from time to time by limiting dilution in order to maintain good levels of antibody production.

Further antibodies useful in ADEPT have been described as follows. Antibody BW 431/26 was described in Haisma, H. J. et al., Cancer Immunol. Immunother., 34: 343–348 (1992). Antibodies L6, 96.5, and 1F5 were described in European Patent 302 473. Antibody 16.88 was described in International Patent Application WO90/07929. Antibody B72.3 was described in European Patent No. 392 745. Antibody CEM231 was described in European Patent No. 382 411. Antibodies HMFG-1 and HMFG-11 (Unipath Ltd, Basingstoke, Hants, United Kingdom) react with a mucin-like glycoprotein molecule on milk fat globule membranes and may be used to target breast and ovarian cancers. Antibody SM3 (Chemicon International Ltd, London, United Kingdom) reacts with core protein of mucin and may be used to target breast and ovarian cancer. Antibodies 85A12 (Unipath Ltd, Basingstoke, Hants, United Kingdom) and ZCEA1 (Pierce Chemical Company, Chester, United Kingdom) react with tumour antigen CEA. Antibody PR4D1 (Serotec, Oxford, United Kingdom) reacts with a colon tumour associated antigen. Antibody E29 (Dako Ltd, High Wycombe, United Kingdom) reacts with epithelial membrane antigen. Antibody C242 is available from CANAG Diagnostics, Gothenberg, Sweden.

Generally, antibodies useful in ADEPT are poorly internalised by the tumour cells they recognise. This allows the targeted prodrug-activating enzyme to be resident on the cell surface and thus generate active drug at the tumour site from circulating prodrug. Internalisation of antibody may be assayed by known techniques, for example as set out in Jafrezou et al., Cancer Research 52: 1352 (1992) and in Press et al., Cancer Research, 48: 2249 (1988).

Large scale purification of CPG2 from *Pseudomonas* RS-16 was described in Sherwood et al (1985), Eur, J. Biochem., 148, 447–453. Preparation of F(ab$^1$)$_2$ and IgG antibodies coupled to CPG enzyme may be effected by known means and has been described for example in PCT WO 89/10140. CPG may be obtained from Centre for Applied Microbiology and Research, Porton Down, Salisbury, Wiltshire SP4 0JG, United Kingdom. CPG2 may also be obtained by recombinant techniques. The nucleotide coding sequence for CPG2 has been published by Minton, N. P. et al., Gene, 31 (1984), 31–38. Expression of the coding sequence has been reported in *E.coli* (Chambers, S. P. et al., Appl. Microbiol, Biotechnol. (1988), 29, 572–578) and in *Saccharomyces cerevisiae* (Clarke, L. E. et al., J. Gen Hicrobiol, (1985) 131, 897–904), Total gene synthesis has been described by M. Edwards in Am. Biotec. Lab (1987), 5, 38–44. Expression of heterologous proteins in *E.coli* has been reviewed by F. A. O. Harston in DNA Cloning Vol. III, Practical Approach Series, IRL Press (Editor D M Glover), 1987, 59–88. Expression of proteins in yeast has been reviewed in Methods in Enzymology Volume 194, Academic Press 1991, Edited by C. Guthrie and G R Fink.

CPG enzyme is available from Sigma Chemical Company, Fancy Road, Poole, Dorset, U.K. CPG enzyme was described in: Goldman, P. and Levy, C. C., PNAS USA, 58: 1299–1306 (1967) and in: Levy, C. C. and Goldman P., J. Biol. Chem., 242: 2933–2938 (1967). Carboxypeptidase G3 enzyme has been described in Yasuda, N. et al., Biosci. Biotech. Biochem., 56: 1536–1540 (1992). Carboxypeptidase G2 enzyme has been described in European Patent 121 352.

According to a further aspect of the present invention we provide a method for the delivery of a cytotoxic drug to a site which comprises administering to a host a first component, which first component comprises an antibody or fragment thereof capable of binding a given antigen, the antibody or fragment thereof being conjugated to a CPG enzyme (preferably carboxypeptidase G2) capable of converting a compound of formula I or physiologically acceptable salt thereof into a cytotoxic drug; followed by administration to the host of a second component, which second component comprises a compound of formula I or a physiologically acceptable salt thereof convertible under the influence of the CPG enzyme (preferably carboxypeptidase G2) to the cytotoxic drug.

The site to which the cytotoxic drug is to be delivered is preferably tumour cells which will generally be present in a tumour-bearing mammalian host such as a human.

When the said first component is administered to the tumour bearing host, the antibody or antibody fragment moiety of the conjugate directs the conjugate to the site of the tumour and binds the conjugate to the tumour cells.

Once unbound conjugate has been substantially eliminated from the host to be treated, for example by clearance from the host after the elapsing of an appropriate time or after accelerated clearance, for example as described in Br. J. Cancer (1990), 61, 659–662, the second component may be administered to the host. It is highly desirable to substantially eliminate unbound conjugate from the host before administration of the second component, since otherwise cytotoxic drug may be generated other than at the site of the tumour thus resulting in general toxicity to the host rather than site specific toxicity.

The compounds of this invention may be utilized in compositions such as tablets, capsules or elixirs for oral administration, suppositories. for rectal administration, sterile solutions or suspensions for parenteral or intramuscular administration, and the like.

The compounds of this invention can be adminstered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 150 mg. per kg per patient per day which can be administered in single or multiple doses. Preferably, the dosage range will be about 10 to 75 mg. per kg per patient per day; more preferably about 10 to 40 mg. per kg per patient per day.

Naturally, these dose ranges can be adjusted on a unit basis as necessary to permit divided daily dosage and, as noted above, the dose will vary depending on the nature and severity of the disease, weight of patient, special diets and other factors.

Typically, these dosages can be formulated into pharmaceutical compositions as discussed below.

About 50 to 500 mg. of compound or mixture of compounds of Formula 1 or a physiologically acceptable salt thereof is compounded with a physiologically acceptable vehicle, carrier, excipient, binder, preservative, stabilizer, flavor, etc., in a unit dosage form as called for by accepted pharmaceutically practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavouring such as cherry or orange flavour.

As discussed above the compounds of formula I and the physiologically acceptable salts thereof as well as the conjugates referred to above may be administered using conventional modes of administration including, but not limited to intravenous, intraperitoneal, oral, intralymphatic or adminstration directly into the tumour. Intravenous administration is preferred, for example intravenous infusion.

Sterile compositions for injection or infusion can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required. Preferred sterile compositions for injection or infusion formulated according to conventional pharmaceutical practice include dissolving the prodrug in a vehicle such as water optionally containing salts, sugar (especially dextran), buffering agents and/or co-solvents (especially polyethylene glycol, propylene glycol or dimethyl isosorbide).

In one embodiment of the present invention, the compound of formula I is provided in the form of the free acid which free acid may then be formulated into a form for parenteral administration immediately prior to administration to the patient. Thus, for example, the compound of formula I in the form of the free acid may be mixed with a buffer whereby it is converted to a physiologically acceptable salt immediately prior to administration.

A preferred unit dosage form of a compound of the present invention comprises a compound of formula I, or a pharmaceutically acceptable salt thereof, in sterile freeze-dried form for reconstitution into injectable/infusable solution in an ampoule. The ampoule preferably contains 500 mg to 2 g (especially 1 g) of said compound.

The following examples illustrate the preparation of the compounds of formula I and their incorporation into pharmaceutical compositions and as such are not to be considered as limiting the invention. In the examples, unless otherwise stated, the following items were standard procedures:

i) All evaporations were carried out by rotary evaporation in vacuo and work-up procedures were carried out after removal of residual solids by filtration;

ii) operations were carried out at room temperature, that is in the range 18–25° C. and under an atmosphere of an inert gas such as argon;

iii) column chromatography (by the flash procedure) was performed on Merck KIESELGEL silica (Art. 9385) obtained from E. Merck, Darmstadt, W. Germany;

iv) yields are given for illustration only and are not necessarily the maximum attainable;

v) the end-products of the formula I have satisfactory microanalyses and their structures were confirmed by NMR and mass spectral techniques;

vi) intermediates were not generally fully characterised and purity was assessed by thin layer chromatographic, infra-red (IR) or NMR analysis;

vii) melting points are uncorrected and were determined using an oil-bath apparatus; melting points for the end-products of the formula I were determined after crystallisation from a conventional organic solvent such as ethanol, methanol, acetone, ether or hexane, alone or in admixture.

EXAMPLE 1

N-(4-[N,N-bis(2-chloroethyl)amino]-phenoxycarbonyl)-L-glutamic Acid

A solution of dibenzyl N-(4-[N,N-bis(2-chloroethyl)-amino]phenoxycarbonyl)-L-glutamate (see (2) in scheme 1) (6 g) in ethyl acetate (100 ml) was hydrogenated over 30% palladium on carbon (0.6 g) for 2 h. When the theoretical amount of hydrogen had been taken up the catalyst was removed by filtration and the filtrate evaporated to dryness. The residue was taken up into hot ether (25 ml) and hexane added until cloudy. On cooling N-(4-[N,N-bis(2-chloroethyl)amino]-phenoxycarbonyl)-L-glutamic acid (see (3) in Scheme 1) was obtained as a white crystalline solid (3.4 g) 79% yield m.p. 87–89°. NMR 7.0 (d) 2H; 6.6 (d) 2H; 6.2 (d) 1H; 4.4 (m) 1H; 3.5–3.7 (m) 8H; 2.0–2.6 (m) 4H.

Elemental Analysis

Expected C=47.2, H=4.95, N=6.88

Found C=47.5, H=5.1, N=6.7.

The titled compound was also prepared in a different polymorphic form, not soluble in ether, with a melting point of 128–130° C.

The starting material dibenzyl N-(4-[N,N-bis(2-chlotoethyl)-amino]phenoxycarbonyl)-L-glutamate was prepared as described below.

A solution of 4-nitrophenyl-chloroformate (1.43 g) in chloroform (15 ml) was added to a mixture of 4-[bis(2-chloro-ethyl)amino]phenol hydrochloride (Biochem. Pharmacol 17 893 (1968)) (1.93 g), triethylamine (2 ml) and chloroform (20 ml). After 2 h at ambient temperature the mixture was evaporated to dryness and the residue chromatographed on Merck silica gel Art 9385. On elution with hexane/ethyl acetate and recrystallisation from benzene:petroleum ether (3:1) the product O-(4-[N,N-bis(2-chloroethyl)amino]-phenyl)-O'-(4-nitrophenyl)carbonate (see (1) in Scheme 1) was obtained as a yellowish solid (1.4 g) (50%) mp=66–7°.

Triethylamine (3.8 ml) was added to 5.5 g of the product so obtained in chloroform (40 ml), followed by addition of L-Glutamic acid dibenzyl ester tosylate (13.75 g). The mixture was stirred and heated at 60° for 4 h and evaporated to dryness. The residue was chromatographed on silica gel (Herck Art 9385) and eluted with 3% ethyl acetate in chloroform to obtain the required starting material dibenzyl-2-([bis(2-chloroethyl)amino]phenoxycarbonyl)glutamate (see (2) in Scheme 1) 6.2 g (77% yield) as a white solid m.p. 85–7°.

EXAMPLE 2

N-(4-[N,N-bis(2-chloroethyl)-amino]-3-methylphenoxycarbonyl)-L-glutamic Acid The process described in Example 1 was repeated using dibenzyl N-(4-[N,N-bis(2-chloroethyl)amino]-3-methyl-phenoxycarbonyl)-L-glutamate in place of dibenzyl N-(4-[N,N-bis(2-chloroethyl)-amino]phenoxycarbonyl)-L-glutamate to obtain N-(4-[N,N-bis(2-chloroethyl)amino]-3-methyl-phenoxycarbonyl)-L-glutamic acid as a white solid, m.p. 160–162° C.

NMR: 7.3 (d) 2H; 6.7 (d) 2H; 6.0 (d) 1H, 4.2 (m) 1H, 3.7 (m) 8H; 2.3–2.0 (m) 4H.

Elemental Analysis

Expected C=47.3; H=5.2; N=10.3; Cl=17.5

Found C=46.8; H=5.2; N=10.3; Cl=18.0.

The dibenzyl N-(-4-[N,N-(2-chloroethyl)amino]-3-methyl-phenoxycarbonyl)-L-glutamate used as starting material was prepared in an analogous manner to that described in Example 1 using 4-[N,N-bis(2-chloroethyl)amino]-3-methyl-phenol in place of 4-[N,N-bis(2-chloroethyl)amino]phenol.

The 4-[N,N-bis(2-chloroethyl)amino]-3-methyl-phenol was obtained as follows (see Scheme 2).

(a) Ethylene oxide (40 g) was bubbled into a solution of 4-amino-m-cresol (12.3 g) in acetic acid/water (1:1) (500 ml). The mixture was allowed to remain at room temperature for 48 h and then evaporated to dryness. The residue was chromatographed on silica gel, eluted with ethyl acetate to obtain 4-[N,N-bis(2-hydroxyethyl)amino]- 3-methylphenol as an oil (6.2 g).

NHR: See Table 2.

(b) Benzyl bromide (4.24 g) was added to a mixture of the product so obtained (6 g), potassium hydroxide (1.6 g) and ethanol (40 ml). The mixture was stirred and heated at reflux for 2 h, cooled and concentrated by evaporation. The residue was poured onto water (100 ml), extracted twice with ethyl acetate, dried and evaporated to obtain 2,2'-(4-benzyloxy-2-toluidino)diethanol as a solid (7.2 g) mp=70–72° C.

NMR: Table 3

(c) Phosphorous pentachloride (11.4 g) was added in portions to the product so obtained (7 g) in chloroform (50 ml) at 10–20° C. The mixture was then heated at reflux for 90 min, cooled and poured onto water. The organic phase was separated and washed with aqueous sodium bicarbonate solution, water and evaporated to dryness. The residue was chromatographed on silica gel. After elution with hexane/ethyl acetate (2:1) 4-benzyloxy-3-methyl-N,N-bis(2-chloroethyl)-aniline (2.2 g) was obtained as an oil.

NMR: See Table 4

An alternative reaction for use in lieu of the reaction immediately above is as follows. Methane sulphonyl chloride (2.5 ml) was added at 0–5° C. to a solution of the product obtained in step (b) (2.6 g) in pyridine (8 ml). The mixture was then heated at 70° C. for 15 min, cooled and poured onto dilute citric acid solution (100 ml). The mixture was extracted twice with ethyl acetate, dried and evaporated to obtain 4-benzyloxy-3-methyl-N,N-bis(2-chloroethyl)-aniline as an oil 2.6 g (84%).

NMR: Table 4.

(d) Ethereal HCl (saturated) was added to the product so obtained (2 g) in ethanol (25 ml) until complete solution was observed. 300 mg of 30% palladium on carbon catalyst was added and the mixture stirred under an atmosphere of hydrogen until the appropriate amount of hydrogen was taken up. The catalyst was removed by filtration and the filtrate evaporated to obtain 4-[N,N-bis(2-chloroethyl)]amino-3-methylphenol hydrochloride as a solid (950 mg) mp=164–7.

EXAMPLE 3

N-(-4-[N,N-bis(2-chloroethyl)amino]phenylcarbamoyl)-L-glutamic Acid Hydrochloride A saturated solution of hydrogen chloride in ether (120 ml) was added to a solution of ditertbutyl N-(-4-[N,N-bis- (2-chloroethyl)amino]-phenylcarbamoyl)-L-glutamate (4.4 g) in ethyl acetate (20 ml). After 1 hour at ambient temperature the mixture was evaporated to a solid. This solid was triturated with ether to obtain N-(4-[N,N-bis(2-chloroethyl)amino]phenylcarbamoyl)-L-glutamic acid hydrochloride (3.5 g) as a grey solid m.p=148–150° C. (see Scheme 3) NMR: 7.2 (d) 2H; 6.7 (d) 2H); 4.2 (n) 1H; 3.7 (m) 8H; 2.4–1.8 (m) 4H;

Elemental Analysis:

Found C=46.7; H=6.8; N=7.0

Expected C=47.1; H=6.5; N=7.5.

The starting material ditertbutyl N-(4-[N,N-bis-[(2-chloroethyl)amino]-phenylcarbamoyl)-L-glutamate was obtained as follows:

A mixture of p-fluoronitrobenzene (14.1 g) and diethanolamine (30 ml) was stirred and heated at 130° C. for 2 h. The mixture was cooled to about 60° C. and poured onto 1 L of water containing 10 ml of 48% caustic soda solution. After cooling to 15° C. a precipitate was filtered off and dried to obtain 2,2'-(4-nitroanilino)diethanol (20.7 g) (92%) m.p.= 102–104° C.

Thionyl chloride (30 ml) was added, with cooling, to a mixture of the product so obtained (20 g), dichloromethane (200 ml) and pyridine (7 ml). After the addition the mixture was heated at reflux for 1 hour. After cooling the mixture was diluted with an equal volume of dichloromethane and carefully washed twice with water, dried and evaporated to obtain [N,N-bis(2-chloroethyl)]-4-nitro-aniline as a solid 21 g m.p.=81–3° C.

To a solution of the product so obtained (0.53 g) in redistilled tetrahydrofuran (20 ml) was added 30% palladium on carbon catalyst (100 mg). The mixture was stirred under an atmosphere of hydrogen for 2 h and the catalyst then removed by filtration. The filtrate was evaporated to dryness and the residue redissolved in ether (20 ml) and a solution of hydrogen chloride gas in ether added to slight excess. The resulting 4-[N,N-bis(2-chloroethyl)amino] anilinium chloride was obtained as a solid and dried. Yield= 0.5 g m.p. 238–40° C. (d).

To a solution of triphosgene (Aldrich) 200 mg in chloroform (10 ml) at 0–5° C., was added the product so obtained (539 mg) followed by triethylamine (0.83 ml). After 15 min at room temperature a solution of L-glutamic acid ditertbutyl ester (0.31 g) in chloroform (5 ml) was added. The mixture was allowed to stand at ambient temperature for 18 h, washed with water, dried and evaporated to dryness. The residue was chromatographed on Merck silica gel and eluted with hexane-ethyl acetate (3:1) to obtain the desired starting material ditertbutyl 4[bis-2-(chloroethylamino)] phenylcarbamoyl-L-glutamate 0.44 g as an oil (see Scheme 3).

NMR:

δ7.2d and δ6.65 (dd)4H. aromatics

δ4.1(m)1H

δ3.66(S)8H

δ1.7–2.2(m)4H

δ1.38(s)9H and δ1.42(s)9H

EXAXPLE 4

N-(-4-[N,N-bis(2-chloroethyl)amino] phenylcarbamoyl)-L-glutamic Acid

An alternative process to that described in Example 3 for preparation of N-(4-[N,N-bis(2-chloroethyl)amino]phenyl-carbamoyl)-L-glutamic acid is described below. The starting material dibenzyl N-(4-[N,N-bis-(2-chloroethyl)amino] phenylcarbamoyl)-L-glutamate was prepared in an analogous manner to the corresponding step in Example 5.

A solution of dibenzyl N-(4-[N,N-bis-(2-chloroetyliamino]-phenylcarbamoyl)-L-glutamate (1.138 g) in DMF (15 ml) was hydrogenated over 10% Pd/C for 16 h. After filtration and evaporation in vacuo, the residue was dissolved in CHCl₃ (20 ml). After 18 h the crystalline precipitate was filte red off and dried in vacuo to obtain N-(4-[N,N-bis-(2-chloroethyl)amino]phenylcarbamoyl)-L-glutamic acid. Yield. 730 mg (93%). After recrystallization from acetone/CHCl₃ microscopic rods formed m.p. 116"118°. NMR (CD₃COCD₃): δ 8.0(s)1H; 7.2(d)2H; 6.6 (d)2H; 6.2(d)2H NH; 4.4(m)1H; 3.6(m)8H; 2.5–1.9(m)4H.

EXAMPLE 5

N-(4-[N,N-bis(2-chloroethyl)-amino]-3-fluorophenylcarbamoyl)-L-glutamic Acid

To a solution of dibenzyl N-(4-[N,N-bis(2-chloroethyl)-amine]-3-fluorophenyl-carbamoyl) L-glutamate (0.4 g) in ethyl acetate (10 ml) was added 30% palladium on carbon (50% moist) (160 mg) and the mixture stirred under an atmosphere of hydrogen for 1 hour. After filtration of the catalyst the filtrate was evaporated to dryness. N-(4-[N,N-bis(2-chloroethyl)-amine]3-fluorophenylcarbamoyl L-glutamic acid was obtained after trituration of the oily residue with ethyl acetate/hexane as a white powder (210 mg, mp 111–114° C.). The starting material dibenzyl N-(4-[N,N-bis(2-chloroethyl)-amino]-3-fluorophenylcarbamoyl) L-glutamic acid was obtained as follows:

A suspension of 4-(N,N-bis-(2-chloroethyl)amino]3-fluoroanilinium oxalate (3.5 g) in anhydrous ethyl acetate (200 ml) and potassium carbonate (5.5 g) was cooled under argon to 5° C. To this mixture was added a solution of phosgene in toluene (1.9M; 5.5 ml). After the addition the mixture was stirred at room temperature for 10 min, filtered and the filtrate dried over magnesium sulphate. The dried filtrate obtained was added in one portion to a mixture of dibenzyl glutamate p toluenesulphonate (5 g), potassium carbonate (2 g) and ethyl acetate (100 ml). Triethylamine (2 ml) was added and the mixture stirred for 20 min at ambient temperature. The zixture was filtered and the filtrate evaporated to dryness. The residue was chromatographed on silica gel eluting with ethyl acetate/hexane (1:2) to obtain the desired starting material as an oil, which crystalized. Yield= 5.5 g m.p. 81–84° C.

4-[N,N-bis(2-chloromethyl)amino]-3-fluoroanilium oxalate was prepared as described in Example 3 except that 3,4 difluoronitrobenzene was used as starting material in place of p-fluoronitrobenzene to obtain 4-[N,N-bis-(2-hydroxyethyl)-amino]fluoronitrobenzene m.p.=99–101° C.

The product so obtained was treated with thionyl chloride as described in Example 3 to obtain 4-[N,N-bis(2-chlotoethyl)-3-fluoronitrobenzene. m.p. 66–8° C.

The product so obtained was hydrogenated as described in Example 3 using ethyl acetate as solvent. The mixture was filtered and the filtrate evaporated to low volume and redissolved in ether. A saturated solution of oxalic acid in ether was added to excess and the desired product 4-[N,N-bis(2-chloromethyl)amino]-3-fluoroanilinium oxalate collected. m.p=146–8° C.

EXAMPLE 6

N-(4-[N,N-bis(2-chloroethyl)amino]-3-chlorophenylcarbamoyl)-L-glutamic Acid

A solution of dibenzyl N-((4[N,N-bis-(2-chloroethyl) amino]3-chlorophenylcarbamoyl))-L-glutamate (350 mg) in ethyl acetate (30 ml) containing 30% palladium on carbon 70 mg (50% moist) was stirred under an atmosphere of hydrogen for 1 hour. After filtration of the catalyst the filtrate was evaporated to dryness and the residue triturated vith ether/ethyl acetate to obtain N-(4-[N,N-bis(2-chloroethyl) amino]-3-chlorophenylcarbamoyl)-L glutamic acid as an oil. NMR: 8.7 (s) 1H; 7.6 (s) 1H; 7.1–7.4 (m) 2H; 6.5 (d) 1H; 4.2 (m) 1H; 3.3–3.6 (m) 8H: 1.7–2.4 (m) 4H.

The starting material dibenzyl 4-[N,N-bis-(2-chloroethyl) amino 3-chlorocarbamoyl)-L-glutamate was obtained by a procedure simralar to Example 3 except that 4-fluoro-3-chloronitrobenzene was used as starting material in place of 4-fluoronitrobenzene to obtain 4[N,N-bis-(2-hydroxyethylamino)]-3-chloro-nitrobenzene as an orange oil. NMR 8.0–8.2 (m) 2H; 7.3 (1) 1H; 4.7 (t) 2H, 3.5(m) 8H.

The product so obtained was treated with thionyl chloride as described in Example 3 to obtain 4[N,N-bis-2 chloroethylamino)-3-chloronitrobenzene as an oil. NMR (CHCl$_3$) 8.3 (d) 1H; 8.1 (q) 1H; 7.25 (d) 1H; 3.8 (t) 4H; 3.6 (t) 4H.

The product so obtained was hydrogenated using ethyl acetate as solvent as described in Example 3. The catalyst was removed by filtration and the filtrate evaporated to low volume, redissolved in ether and saturated ethereal oxalic acid added to excess. The oxalate salt was obtained by filtration m.p.=118–21° C.

The product so obtained was converted to dibenzyl N-(4 [N,N-bis-(2-chloroethyl)amino]-3-chlorophenylcarbamoyl)-L-glutamic acid as described in Example 5. An oil was obtained; NMR 7.1–7.4 (m) 13H; 5.1 (s) 2H; 5.0 (s) 2H; 4.6 (m) 1H; 3.5 (s) 8H; 2.0–2.6 (m) 4H.

EXAMPLE 7

Typical pharmaceutical compositions containing a compound of the invention

| A: Dry Filled Capsules Containing 100 mg of Prodrug Per Capsule | |
|---|---|
| Ingredient | Amount per capsule (mg) |
| Compound | 100 |
| Lactose | 149 |
| Magnesium stearate | 1 |
| Capsule (size No 1) | 250 |

The compound can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain compound (100 mg), pregelatinized starch USP (82 mg), microcrystalline cellulose (82 mg) and magnesium stearate (1 mg).

C: Suppository

Typical suppository formulations for rectal administration can contain compound (50 mg), disodium calcium edetate (0.25–0.5 mg). and polyethylene glycol (775–1600 mg). Other suppository formulations can be made by substituting, for example butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol.

D: Injection

A typical injectible formulation would contain compound (500 mg) benzylalcohol (0.05 ml) and 0.15M sodium bicarbonate for injection (5.0 ml).

EXAMPLE 8 (see Scheme 4)

N-(4-[N-(2-chloroethyl)-N-(2-mesyloxyethyl)amino] phenoxy-carbonyl)-L-glutamic Acid N-(4-([N-(2-chloroethyl), N-(2-mesyloxyethyl)]amino)-phenyloxycarbonyl)-L-glutamic acid-di-t-butyl ester (6, wherein $R^1$—Cl and $R^2$=OSO$_2$Me) (110 mg) was suspended in trifluoroacetic acid (TFA) (2.2 ml) and stirred for 40 min at ambient temperature. TFA was removed under reduced pressure; the remaining oil was diluted with ethyl acetate (1 ml) and evaporated to obtain N-(4-[N-(2-chloroethyl)-N-(2-mesyloxyethyl)amino] phenoxycarbonyl)-L-glutamic acid–1.02 TFA–0.16 EtOAc (9, wherein $R^1$=Cl and $R^2$—OSO$_2$Me), 90 mg, 95% yield.

NMR: —CH$_2$—CH$_2$—OSO$_2$Me/—CH$_2$—CH$_2$Cl 3.15 (s), 3H; 3.70 (m) 6H; Other 4.30 (t) 1H; 4.49 (t) 1H; Aromatics 6.75 (d) 2H; 6.92 (d) 2H; 1.8–2.3 (m) 4H; 4.02 (m) 1H; 7.90 (d) 1H.

The starting material 4-([N-(2-chloroethyl),N-(2-mesyloxy-ethyl)]amino)phenyloxycarbonyl-L-glutamic acid-di-t-butyl ester was prepared as described below.

A solution of L-glutamic acid di-t-butyl ester hydrochloride (4.26 g) and triethylamine (4 ml) in dry chloroform (30 ml) was stirred with a cooled solution of 4-nitrophenylchloroformate (2.92 g, available from Aldrich) for 5 min. After 5 hours at ambient temperature, the solvent was evaporated and the residue dissolved in ethyl acetate (70 ml), filtered and evaporated to dryness. The residue was chromatographed on silica gel; eluted with chloroform to obtain 4-nitrophenyloxycarbonyl-L-glutamic acid di-t-butyl ester (2) as an oil, 5.02 g (82%).

NMR: 7.33 (d) 2H; 8.24 (d) 2H; 1.46 (s) 9H; 1.50 (s) 9H; 2.0–2.4 (M) 4H; 4.32 (m) 1H; 5.90 (d) 1H.

A solution of the product so obtained (2) (5.01 g) in acetic acid (30 ml) was hydrogenated over 10% palladium on carbon for three days. After filtering, the solution was cooled and ethylene oxide (5 ml) added, and left at ambient temperature for 22 hours. Solvent was evaporated and the residue was partitioned between ethyl aceate and water. The organic phase was separated, washed with water, dried (Na$_2$SO$_4$) and evaporated to dryness. The residue was chromatographed on silica gel; eluted with ethyl acetate in chloroform (2:1) to obtain 4-[bis(2-hydroxyethyl)amino] phenyloxycarbonyl-L-glutamic acid di-t-butyl ester (4) (3.93 g) 69% m.p. 91–93° C.

A solution of the product so obtained (4) (0.86 g) in pyridine (3 ml) was stirred with methanesulphonyl chloride (0.6 ml) at 2° C. for 20 min, followed by 50° C. for 10 min. The reaction mixture was partitioned between ethyl acetate and water. The organic phase was separated, washed with water, dried (Na$_2$SO$_4$) and evaporated to dryness. The residue was chromatographed on silica gel; eluted with ethyl acetate in dichloromethane (1:9) to obtain 4-[(2-chloroethyl) [2-(mesyloxy)ethyl]aminophenyloxycarbonyl-L-glutamic acid-di-t-butyl ester (6) as an oil (0.44 g) 43%.

NMR: 3.15 (s) 3H; 3.70 (m) 6H; 4.29 (t) 2H; 6.75 (d) 2H; 6.92 (d) 2H; 1.41 (s) 9H; 1.42 (s) 9H; 1.8–2.3 (m) 2H; 3.97 (m), 1H; 7.92 (d) 1H.

EXAMPLES 9–15

The following compounds listed in Table 1 were prepared according to Example 2 using the starting materials and intermediates listed in Tables 2–8 below:

TABLE 1

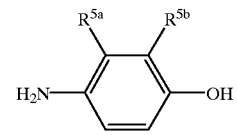

| Ex No | R⁵ᵃ⁻ᵇ | mpt | ClCH₂CH₂M— | Aromatics | αCH | —CH₂CH₂— | Other |
|---|---|---|---|---|---|---|---|
| 9 | $CH_3(R^{5a})$ | 160–2° C. | 3.34–3.54(m)8H | 6.9–7.22(m)3H; | 4.1(m)1H | 2.0–2.5(m)4H | 2.27(s)3H $CH_3$ |
| 10 | $Pr^i(R^{5a})$ | 156–8° C. | 3.32–3.55(m)8H | 6.95–7.28(m)3H; | 4.1(m)1H | 2.0–2.49(m)4H | 3.7(m)1H CH 1.14(d)2H$(CH_3)_2$ |
| 11 | $CH_3(R^{5b})$ | 124–6° C. | 3.7(m)8H | 6.5–6.9(m)3H | 4.1(m)1H | 1.9–2.3(m)4H | 2.1(s)3H $CH_3$ |
| 12 | $F(R^{5a})$ | | 3.6(m)8H | 6.8–7.2(m)3H | 4.1(m)1H | 2.0–2.49(m)4H | |
| 13 | —CH=CH—CH=CH— $(R^{5a-b})$ | | 3.6(m)8H | 6.6–8.0(m)6H | 4.2(m)1H | 2.1–2.5(m)4H | |
| 14 | $Cl(R^{5b})$ | 106–8° C. | 3.6(m)8H | 6.7–7.1(m)3H | 4.1(m)1H | 1.9–2.4(m)4H | |
| 15 | $Cl(R^{5a})$ | 148–150° C. | 3.4–3.54(m)8H | 7.0–7.4(m)3H) | 4.1(m)1H | 1.9–2.36(m)4H | |

Thus the compounds of Examples 9–15 were prepared in an analogous manner to that described in Example 2. The compound of Example 10 was thus prepared by substituting 4-amino-3-isopropylphenol (Gilman, H, et al., J. Org. Chem. 19, (1954) 1067–78 for 4-amino-m-cresol used in step (a). The compound of Example 11 was prepared by substituting 4-amino-2-methylphenol (available from Aldrich) for 4-amino-m-cresol and the compound of Example 12 was prepared by substituting 4-amino-3-fluorophenol (prepared according to Journal of the Chemical Society (1964) p473) for 4-amino-m-cresol. The compound of Example 13 was prepared by substituting 4-aminonaphth-1-ol (Aldrich Chemical Co Ltd) for 4-amino-m-cresol and the compound of Example 14 was prepared by substituting 4-amino-2-chlorophenol (prepared according to Journal of the American Chemical Society 45, 2192, (1923)) for 4-amino-m-cresol. The compound of Example 15 was prepared by substituting 4-amino-3-chloro-phenol (Berichte; p. 2065 (1938); and Organic Synthesis; Collected Vol 4, p. 148) for 4-amino-m-cresol.

The starting materials and intermediates employed in the preparation of Examples 9–15 and their properties are listed in Tables 2–8 below:

TABLE 2

| R⁵ᵃ or ᵇ | m.p. or NMR data | Reference |
|---|---|---|
| Me $(R^{5a})$ | 176–9° C. | Aldrich |
| $Pr^i$ $(R^{5a})$ | 172–5° C. | |

TABLE 2-continued

| R⁵ᵃ or ᵇ | m.p. or NMR data | Reference |
|---|---|---|
| Cl $(R5_a)$ | 6.5–6.7(m)3H Aromatics; 8.8(s)1H OH; 4.6(br s)2H $NH_2$; 159.5° C. | J. Chem. Soc. (1928), 2703 |
| He $(R5^b)$ | 174–6° C. | Aldrich |
| Cl $(R5_b)$ | 146–8° C. | |
| F $(R5_a)$ | 6.6–6.9(m)3H Aromatics; 9.4(s)1H OH; 4.4(m)2H $NH_2$ | |
| $DiCH_3$ $(R5^a = R5^b = CH_3)$ | 260–2° C. (as hydrochloride ex Aldrich) | |
| ($R5^a$ and $R5^b$ together represent —CH=CH—CH=CH—) | 273° C. (as hydrochloride ex Aldrich) | |

TABLE 3 structure: HO-CH2CH2-N(-CH2CH2-OH)-C6H2(R5a)(R5b)-OH

| R5a-b | HOCH$_2$CH$_2$N— | Aromatics | Other |
|---|---|---|---|
| Me (R$^{5a}$) | 2.8–3.3 (m) 8H | 6.4–6.9 (m) 3H | 2.03(s)3H CH$_3$ |
| Pr$^i$ (R$^{5a}$) | 3.0–3.4 (m) 8H | 6.6–7.1 (m) 3H | 3.6(m)1H; 1.1(d)6H Pr$^i$ |
| Cl (R$^{5a}$) | 3.15–3.54 (m) 8H | 6.7–7.2 (m) 3H | |
| CH$_3$ (R$^{5b}$) | 3.3–3.5 (m) 8H | 6.4–6.6 (m) 3H | 2.06(s)3H CH$_3$ |
| Cl (R$^{5b}$) | 3.2–3.6 (m) 8H | 6.5–6.8 (m) 3H | |
| F (R$^{5a}$) | 3.1–3.4 (m) 8H | 6.5–6.9 (m) 3H | |
| di CH$_3$ (R$^{5a}$ = R$^{5b}$ = CH$_3$) | 2.9–3.4 (m) 8H | 6.6–7.0 (m) 3H | 2.0(s)3H; 2.2(s)3H CH$_3$ |
| (R$^{5a}$ and R$^{5b}$ together represent —CH=CH—CH=CH—) | 3.2–3.4 (m) 8H | 6.8–8.3 (m) 11H | |

TABLE 4 structure: HO-CH2CH2-N(-CH2CH2-OH)-C6H2(R5a)(R5b)-O-CH2-Ph

| R5a-b | HOCH$_2$CH$_2$N— | Aromatics | —CH$_2$— | Other |
|---|---|---|---|---|
| Me (R$^{5a}$) | 3.0–3.2 (m) 8H | 6.8–7.5 (m) 8H | 5.0(s) 2H | 2.2(s)3H; CH$_3$ |
| Pr$^i$ (R$^{5a}$) | 2.9–3.3 (m) 8H | 6.8–7.5 (m) 8H | 5.0(s) 2H | 3.6(m)1H; 1.1(d)6H Pr$^i$ |
| Cl (R$^{5a}$) | 3.05–3.35 (m) 8H | 6.9–7.5 (m) 8H | 5.1(s) 2H | 2.2(s)3H CH$_3$ |
| CH$_3$ (R$^{5b}$) | 31–3.4 (m) 8H | 6.9–7.3 (m) 8H | 5.0(s) 2H | |
| Cl (R$^{5b}$) | 3.3–3.5 (m) 8H | 6 8–7.4 (m) 8H | 5.0(s) 2H | |
| F (R$^{5a}$) | 3.2–3.4 (m) 8H | 6.8–7.5 (m) 8H | 5.0(s) 2H | |
| Di CH$_3$ (R$^{5a}$ = R$^{5b}$ = CH$_3$) | 2.9–3.3 (m) 8H | 6.8–7.4 (m) 8H | 5.0(s) 2H | 2.2(s)3H; 2.1(s)3H CH$_3$ |
| (R$^{5a}$ and R$^{5b}$ together represent —CH=CH—CH=CH—) | 3.2–3.4 (m) 8H | 6.9–8.3 (m) 6H | 5.3(s) 2H | |

TABLE 5 structure: R1-CH2CH2-N(-CH2CH2-R2)-C6H2(R5a)(R5b)-O-CH2-Ph

| R5a-b | R$^1$ | R$^2$ | —CH$_2$CH$_2$N— | —CH$_2$— | Aromatics | Other |
|---|---|---|---|---|---|---|
| Me(R$^{5a}$) | Cl | Cl | 3.3–3.5 (m) 8H | 5.08(s) 2H | 6.8–7.4 (m) 8H | 2.3 (s) 3H He |
| Pr$^i$(R$^{5a}$) | Cl | Cl | 3.2–3.5 (m) 8H | 5.04(s) 2H | 6.8–7.4 (m) 8H | 3.7(m)1H; 1.1(d)6H |
| Cl(R$^{5a}$) | Cl | Cl | 3.4–3.6 (m) 8H | 5.1(s) 2H | 6.9–7.4 (m) 8H | |
| CH$_3$(R$^{5b}$) | Cl | Cl | 3.3–3.6 (m) 8H | 5.1(s) 2H | 6.9–7.4 (m) 8H | |
| Cl(R$^{5b}$) | Cl | Cl | 3.6 (m) 8H | 5.1(s) 2H | 6.8–7.4 (m) 8H | |
| F(R$^{5b}$) | Cl | Cl | 3.4–3.6 (m) 8H | 5.06(s) 2H | 6.8–7.4 (m) 8H | |
| Di CH (R$^{5a}$ = R$^{5b}$ = CH$_3$) | Cl | Cl | 3.2–3.5 (m) 8H | 5.06(s) 2H | 6.8–7.4 (m) 7H | 2.2(s)3H; 2.1(s)3H CH$_3$ |

TABLE 5-continued

[Structure: Aniline with N(CH2CH2R1)(CH2CH2R2), R5a and R5b on ring, O-CH2-Ph substituent]

| R5a-b | R1 | R2 | —CH2CH2N— | —CH2— | Aromatics | Other |
|---|---|---|---|---|---|---|
| (R5a and R5b together represent —CH=CH—CH=CH—) | Cl | Cl | 3.4–3.7 (m) 8H | 5.3(s) 2H | 7.1–8.3 (m) 11H | |

TABLE 6

[Structure: 4-[bis(2-chloroethyl)amino]phenol with R5a and R5b substituents]

| R5a-b | m.p. of HCl salt (° C.) |
|---|---|
| Pr$^i$ (R5a) | 124–7 |
| Me (R5a) | 164–7 |
| Me (R5b) | 122–4 |
| Cl (R5b) | 156–8 |
| F (R5a) | 123–5 |
| (R5a = R5b = CH3) di-CH3 | 144–6 |
| (R5 and R5b together represent —CH=CH—CH=CH—) | 180–4 |
| Cl (R5a) | 119–121 |

TABLE 7

[Structure: 4-[bis(2-chloroethyl)amino]phenyl 4-nitrophenyl carbonate]

| R5a-b | —ClCH2CH2N— | aromatics | other |
|---|---|---|---|
| CH3(R5a) | 3.57(m)4H; 3.35(m)4H | 7.2–8.4(m)7H | 2.32(s)3HCH3 |
| Pr$^i$(R5a) | 3.5(m)4H; 3.34(m)4H | 7.2–8.4(m)7H | 3.7(m)1HCH; 1.1(d)2H(CH3) |
| CH3(R5b) | 3.7(m)4H; 3.32(m)4H | 6.7–8.4(m)7H | 2.2(s)3HCH3 |
| 3F | 3.5–3.7(m)8H | 7.2–8.1(m)7H | |
| 1,4 Naphth | 3.5–3.5(m)8H | 7.2–8.4(m)10H | |
| 2Cl | 3.75(m)8H | 6.7–8.4m(7H) | |

TABLE 8

[Structure: carbamate with glutamate dibenzyl ester attached via O-C(=O)-NH to phenyl with N(CH2CH2Cl)2 and R5a, R5b substituents]

| R5a-b | —ClCH2CH2N— | Aromatics | ArCH2O | αCH | —CH2CH2— | other |
|---|---|---|---|---|---|---|
| CH3(R5a) | 3.42(m)8H | 7.35–6.9(m)13H | 5.2(s)2H 5.1(s)2H | 4.4(m)1H | 2.5–2.1(m)4H | 2.3(s)3HCH3 |
| Pr$^i$(R5a) | 3.5(m) 3.3(m)8H | 7.35–6.7(m)13H | 5.2(s)2H 5.1(s)2H | 4.3(m)1H | 2.5–2.1(m)4H | 3.6(m)1HCH 1.1(d6H 2xCH3 |
| CH3(R5b) | 3.7(m) 3.3(m)8H | 6.6–7.4(m)13H | 5.14(s)2H 5.09(s)2H | 4.2(m)1H | 2.5–2.1(m)4H | 2.1(s)3H CH3 |
| 3F | 3.60(m)8H | 6.7–7.4(m)13H | 5.13(s)2H 5.08(s)2H | 4.2(m)1H | 2.5–2.1(m)4H | |

TABLE 8-continued

[Structure: Cl-CH₂-CH₂-N(CH₂-CH₂-Cl)- attached to a benzene ring bearing R^5a and R^5b, connected via -O-C(=O)-NH-CH(COOBz)-CH₂-CH₂-COOBz]

| R^5a-b | —ClCH₂CH₂N— | Aromatics | ArCH₂O | αCH | —CH₂CH₂— | other |
|---|---|---|---|---|---|---|
| 1,4 Naphthyl | | 7.1–8.4(m)16H | 5.1(s)2H<br>5.16(s)2H | 4.2(m)1H | 2.5–2.1(m)4H | |
| 2Cl | 3.7(m)8H | 6.7–7.4(m)13H | 5.09(s)2H<br>5.15(s)2H | 4.2(m)1H | 2.5–2.1(m)4H | |
| Cl(R5^a) | 3.45–3.62(m)8H | 6.98–7.36(m)13H | 5.09(s)2H<br>5.16(s)2H | 4.2(m)1H | 2.1–2.5(m)4H | |

EXAMPLE 16

N-(4-[N,N-bis(2-chloroethyl)amino]phenoxycarbonyl)-L-glutamic Acid-γ-anilide A suspension of α-benzyl 4-[N,N-bis(2-chloroethyl)amino]-phenoxycarbonyl-L-glutamic acid-γ-anilide (2.0 g) in ethyl acetate (50 ml) was hydrogenated over 10% palladium on carbon (0.15 g) for 4 h. The catalyst was removed by filtration and the filtrate was evaporated to dryness under reduced pressure at 35°. The product, 4-[N,N-bis(2-chloroethyl)amino]phenoxycarbonyl-L-glutamic acid-γ-anilide (1 in Scheme 6) was obtained as a white crystalline solid, 1.4 g (83%) m.p. 110°.
Elemental Analysis
  % Expected C=54.8, H=5.22, N=8.71
  % Found C=54.5, H=5.62, N=8.31.

The starting material, α-benzyl-4-[N,N-bis(2-chloroethyl)amino]phenoxycarbonyl-L-glutamic acid γ-anilide, was prepared as described below.

Triethylamine (2 mls) was added to a mixture of alpha-benzyl-p-tosyl-L-glutamic acid γ-anilide (2.8 g) and O-(4-[N,N-bis(2-chloroethyl)amino]phenyl-O'-(4-nitrophenyl)carbonate (2.0 g) in dichloromethane (30 mls). The mixture was stirred at room temperature for 16 hours and the solvents were removed in vacuo. The residue was chromatographed on silica gel (Herck Art 9385) and eluted with 10% ethyl acetate in dichloromethane to give α-benzyl-4-[N,N-bis(2-chloroethyl)amino]phenoxycarbonyl-L-glutamic acid γ-anilide as a white solid, 1.9 g (64%).

The starting material O-(4-[N,N-bis(2-chloroethyl)-amino]phenyl-O'-(4-nitrophenyl)carbonate was prepared as described below.

A solution of triethylamine (10 mls) in dichloromethane (10 mls) was added to a mixture of 4-nitrophenyl-chloroformate (7.25 g) and 4-(N,N-bis(2-chloroethyl)amino)phenol hydrochloride (10 g) in dichloromethane (100 mls) over a period of two hours. After stirring at room temperature for 16 h the solvents were removed under reduced pressure and the residue was chromatographed on silica gel (Merck Art. 9385). Elution with dichloromethane and evaporation of the eluates yielded the product as a red oil. Trituration with hexane gave a yellow solid which was recrystallised from benzene/hexane to give O-(4-[N,N-bis(2-chloroethyl)amino)phenol-O'-(4-nitrophenyl)carbonate as orange crystals, 10.4 g (71%). m.p. 68°.

The starting material p-tosyl-α-benzyl-L-glutamic acid γ-anilide was prepared as described below.

N-t-BOC-L-glutamic acid α-benzyl ester (10 g) and dicyclohexylcarbodiimide (6.1 g) were dissolved in dichloromethane (120 mls) and stirred at room temperature for 10 minutes. Aniline (2.8 mls) was added and the mixture stirred at room temperature for 16 hours. The mixture was filtered and the precipitate washed with dichloromethane (2×15 mls). The filtrate was washed successively with saturated NaHCO₃ solution (2×100 mls) and water (100 mls) then evaporated. The resulting solid was recrystallised from EtOAc/hexane to give colourless plates, 8.2 g (67%). The γ-anilide (12.0 g) and p-toluenesulphonic acid (5.4 g) in benzene (300 mls) were refluxed for 40 minutes and allowed to cool overnight. The precipitate was filtered, dried at the pump and recrystallised from EtOAc/MeOH to give colourless plates of tosyl-α-benzyl-L-glutamic acid γ-anilide, 8.2 g (58%).

EXAMPLE 17

N-(4-[N,N-bis(2-chloroethyl)amino]phenoxycarbonyl)-L-glutamic Acid-γ-t-butylamide The process described in Example 16 was repeated using α-benzyl 4-[N,N-bis(2-chloroethyl)amino]phenoxycarbonyl-L-glutamic acid-γ-t-butylamide in place of α-benzyl 4-[N,N-bis(2-chloroethyl)amino]phenoxycarbonyl-L-glutamic acid-γ-anilide to obtain 4-[N,N-bis(2-chloroethyl)amino]phenoxycarbonyl-L-glutamic acid-γ-t-butylamide (2 in Scheme 6), which was recrystallised from ethyl acetate/hexane to give colourless crystals, m.p. 129°.
Elemental Analysis
  % Expected C=51.9, H=6.32, N=9.09
  % Found C=52.1, H=6.33, N=8.96.

The α-benzyl 4-[N,N-bis(2-chloroethyl)amino]phenoxycarbonyl-L-glutamic acid-γ-t-butylamide was obtained in an analogous manner to that described in Example 16 for the γ-anilide derivative.

EXAMPLE 18

N-(4-[N,N-bis(2-chloroethyl)amino]-3-methylphenylcarbamoyl)-L-glutamic Acid

A solution of di-t-butyl 4-[N,N-bis(2-chloroethyl)amino]-3-methylphenylcarbamoyl-L-glutamate (0.6 g) in dichloromethane (6 ml) was cooled to 0° C., trifluoroacetic acid (15 ml) was added. This solution was then left at 0° C. for 3 days. The solution was then evaporated to dryness to yield (4-[N,N-bis(2-chloroethyl)amino]-3-methylphenylcarbamoyl-L-glutamic acid as an oil. Yield 0.49 g.

NMR: 8.46(s)1H); 7.15(m)3H; 6.4(d)1H; 4.18(m)1H; 3.55(m)4H; 3.35(m)4H; 2.3(m)2H; 2.23(s)3H, 2.0(m)2H.

The starting material di t-butyl 4-[N,N-bis(2-chloroethyl)-amino]-3-methylphenylcarbamoyl-L-glutamate was prepared as described below:

Potassium carbonate (27.5 g) was added to a solution of 3-methyl-4-nitroaniline (Journal of Organic Chemistry 33, 3498 (1968) (7.6 g) in ethyl acetate (150 ml), followed by dropwise addition of a 1.9M solution of phosgene in toluene (27.5 ml) maintaining the temperature below 30° C. The mixture was then stirred at ambient temperature for 1 hour. L-glutamic acid di-t-butyl ester (13 g) was added to the mixture which was then stirred at ambient temperature overnight. The solution was then filtered, washed with water, and the organic layer dried over $MgSO_4$ and evaporated to an oil. This was then chromatographed on silica, eluted with Hexane: ethyl acetate 3:1 to give di t-butyl(3-methyl-4-nitrophenylcarbamoyl-L-glutamate as an oil. Yield=11.19 g 51%). NMR: 9.16(s)1H; 8.0(d)1H; 7.43(m) 2H; 6.70(d)1H; 4.1(m)1H, 2.51(s)3H; 2.25(m)2H; 1.8(m) 2H; 1.41(d)8H.

A solution of di t-butyl 3-methyl-4-nitrophenyl-carbamoyl-L-glutamate (4.7 g) in ethyl acetate (125 ml) was hydrogenated over 30% Pd/C (0.5 g). The mixture obtained was then filtered through CELITE (a purified and calcined diatomaceous earth-particle size 20–45 um obtainable inter alia from Fluka Chemicals Ltd) and evaporated to a dark solid. This solid was chromatographed on silica eluted using ethyl acetate:hexane (1:1) to give di t-butyl 3-methyl-4-aminophenylcarbamoyl-L-glutamate as in oil yield=3.71 g 83%. NMR: 7.98(s)1H; 6.9(m)2H; 6.52(d)1H; 6.15(d)1H; 4.53(s)2H; 4.15(m)1H; 2.25(m)2H; 2.04(s)3H; 1.8(m)2H; 1.45(d)18H.

Ethylene oxide (4.8 g) was bubbled through a solution of di t-butyl 3-methyl-4-aminophenylcarbamoyl-L-glutamate (5 g) in glacial acetic acid (25 ml) and $H_2O$ (25 ml). The solution was then stirred at ambient temperature for 24 hours. After evaporation to dryness, the residue was redissolved in ethyl acetate, washed with water, the organic layer dried over $MgSO_4$ and evaporated to yield di t-butyl 4-[N,N-bis(2-hydroxyethyl)amino]-3-methylphenylcarbamoyl-L-glutamate which was used without further purification. NMR: 8.35(s)1H; 7.1(m)3H; 6.35(d)1H; 4.15(m)1H; 3.35 (m)4H; 3.05(m)4H; 2.25(m)2H; 2.20(s)3H; 1.8(m)2H; 1.45 (d)18H.

Methanesulfonyl chloride (3.8 ml) was added dropwise to a solution of di t-butyl 4-[N,N-bis(2-hydroxyethyl)amino]-3-methylphenylcarbamoyl-L-glutamate (4 g) in pyridine (60 ml) under an argon atmosphere maintaining the temperature below 30° C. After addition, the solution was stirred at 80° C. for 2 hours. The solution was cooled and poured onto 10% citric acid (500 ml), extracted with ethyl acetate, washed with water, the organic layer dried over $MgSO_4$ and then evaporated to a brown oil. This oil was chromatographed on silica eluted using 5:1 hexane:ethyl acetate to give di t-butyl 4-[N,N-bis(2-chloroethyl)amino]-3-methylphenylcarbamoyl-L-glutamate as an oil. Yield=7.23 g. 28%. NMR: 8.42(s)1H; 7.1(m)3H; 6.36(d)1H; 4.13(m) 1H; 3.50(m)4H; 3.31(m)4H); 2.3(m)2H; 2.23(s)3H; 1.9(m) 2H; 1.4(s)9H; 1.35(s)9H.

The reaction sequence for this Example appears in Scheme 7.

EXAMPLE 19

N-(4-[N,N-bis(2-chloroethyl)amino] benzylcarbonyl)-L-glutamic Acid

Di t-butyl 4-[N,N-bis(2-chloroethyl)amino] benzylcarbonyl-L-glutamate (0.5 g) was dissolved in $CH_2Cl_2$ (1.5 ml) and trifluoroacetic acid (1.5 ml) was added. The solution was stirred at ambient temperature for 2 hours. The solution was then evaporated to give the title compound as an oil (0.8 g). NMR: 8.22(d)1H; 7.10(d)2H; 6.66(d)2H; 4.19(m)1H; 3.69(s)8H; 2.24(m)2H; 1.9(m)2H; 3.32(s)2H.

The starting material di t-butyl 4-[N,N-bis(2-chloroethyl) amino]benzylcarbonyl-L-glutamate was prepared as described below:

1-Hydroxybenzotriazole (4.05 g) was added to a solution of 4-nitrophenyl acetic acid (5.4 g) in dimethylformamide (75 ml). L-Glutamic acid di tert-butyl ester (7.77 g) and then dicyclohexylcarbodiimide (6.2 g) were added to the mixture. The mixture was then stirred for 18 hr at ambient temperature. The mixture was filtered and the filtrate washed with saturated sodium bicarbonate solution, water and 0.5 m hydrochloric acid and then dried and evaporated to dryness. The residue was chromatographed on silica gel by eluting with hexane/ethyl acetate (2:1) to give di t-butyl 4-nitrobenzylcarbonyl-L-glutamate as an oil 9.7 g (77%). NMR: 8.2(d)2H; 7.45(d)2H; 6.45(d)1H; 4.45(m)1H; 3.15(s) 2H; 2.1(m)4H; 1.4(d)9H; 1.35(s)9H.

A solution of di t-butyl 4-nitrobenzylcarbonyl-L-glutamate (9.7 g) in ethyl acetate (200 ml) was hydrogenated over 30% Pd/C (900 mg). The mixture was then filtered through Celite and evaporated to yield a yellow oil (di t-butyl 4-aminobenzylcarbonyl-L-glutamate) which was used without further purification. NMR: 8.23(d)1H; 6.92(d) 2H; 6.50(d)2H; 4.86(s)2H; 4.15(m)1H; 3.24(s)2H; 2.22(m) 2H; 1.8(m)2H); 1.4(d)18H. Yield 8.2 g 90%.

Ethylene oxide (7.1 g) was added to a solution of di t-butyl 4-aminobenzylcarbonyl-L-glutamate (8.2 g) in glacial acetic acid (40 ml) and $H_2O$ (40 ml). The mixture was then stirred at ambient temperature for 24 hours. The solution was evaporated to dryness redissolved in ether, washed with $H_2O$, the organic layer dried over $MgSO_4$ and evaporated to an oil, (di t-butyl 4-[N,N-bis(2-hydroxyethyl) amino]-benzylcarbonyl-L-glutamate) (6.3 g) which was used without further purification. (6.3 g). NMR: 8.16(d)1H; 7.02(d)2H; 6.58(d)2H; 4.1(m)1H; 3.4(m)8H; 3.25(s)2H; 2.25(m)2H; 1.8(m)2H; 1.4(s)18H.

Methanesulfonyl chloride (2.91 ml) was added dropwise to a solution of di t-butyl 4-[N,N-bis(2-hydroxyethyl)amino] benzylcarbonyl-L-glutamate (2.88 g) in pyridine (45 ml) under an argon atmosphere, maintaining the temperature below 25° C. After the addition the solution was stirred at 80° C. for 1 hour. The solution was then cooled and poured onto 10% citric acid (500 ml) extracted into ether, washed with water, the organic layer was dried over $MgSO_4$ and then evaporated to a brown oil. This oil was chromatographed on silica eluting with hexane: ethyl acetate 2:1 to give di t-butyl 4-[N,N-bis(2-chloroethyl)amino] benzylcarbonyl-L-glutamate as an oil (1.3 g) (42%). NMR: 8.19(d)1H; 7.10(d)2H; 6.66(d)2H; 4.10(m)1H; 3.69(s)8H; 3.32(s)2H; 2.21(m)2H; 1.9(m)2H; 1.37(d)18H. Yield 1.32 g 42%.

The reaction sequence for this Example appears in Scheme 8.

EXAMPLE 20

N-(4-[N,N-bis-(2-chloroethyl)amino] phenylcarbamoyl)-L-glutamic Acid

A solution of di t-butyl 4-[N,N-bis-(2-chloroethyl)-amino]phenylcarbamoyl-L-glutamate (prepared as described in Example 3) (500 mg) in 98% formic acid (10 ml) was allowed to stand at ambient temperature for 24 h.

EXAMPLE 21

N-(4-N,N-bis(2-bromoethyl)amino]-3-fluorophenylcarbamoyl)-L-glutamic Acid

A solution of dibenzyl 4[N,N-bis(2-bromoethyl)amino-3-fluorophenyl-carbamoyl-L-glutamate (0.5 g) in ethyl acetate (10 ml) and 30% Pd/C (100 mg) was stirred under an atmosphere of hydrogen for 6 hr. The catalyst was filtered off and the filtrate evaporated to an oil to give the title compound. NMR: 8.6(s)1H; 7.35(dd)1H; 7.1–6.8(m)2H; 6.5(d)1H; 4.2(m)1H; 3.7–3.2(m)8H; 2.4–1.6(m)4H.

The starting material for this reaction was prepared in an analogous manner to that set out in Example 5 but thionyl bromide was used in place of thionyl chloride.

TABLE 9

| Ex No | X | R | M.pt |
|---|---|---|---|
| 22 | Cl | F | 111–114° C. |
| 23 | Cl | Cl | oil |
| 24 | Cl | CN | 105–7° C. |

The NMR data for the compound of Example 23 is as follows: δ8.6(broad)1H, δ7.6(m)1H, δ7.2(m)2H, δ4.25(m)1H; δ3.6–3.3(m)8H; δ2.4–1.7(m)4H.

The starting materials and intermediates used in the preparation of the compounds of Examples 21–24 and their properties are listed in Tables 10–13 below:

TABLE 10

| R | m.p |
|---|---|
| F | 99–101 |
| Cl | Oil |
| CN | 151–4 |

*NMR(DHSOd$_6$) 8.15(d)1H: 8.05(q)1H; 7.3(d)1H; 4.65(t)2H(OH); 3.5(m)8H.

TABLE 11

| X | R | m.p. |
|---|---|---|
| Cl | F | 66–8° C. |
| Cl | Cl | Oil* |
| Cl | CN | 106–9 |
| Br | F | 66–68° C. |

*NMR(CDCl$_3$): 8.3(d)1H; 8.1(q)1H; 7.25(d)1H; 3.75(t)4H; 3.6(t)4H.

TABLE 12

| X | R | m.p. (of oxalate salt) |
|---|---|---|
| Cl | F | 146–8° C. |
| Cl | Cl | 118–21° C. |
| Cl | CN | 112–6° C. |
| Br | F | 134–6° C. |

TABLE 13

| X | R | m.p. |
|---|---|---|
| Cl | F | 81–4° C. |
| Cl | Cl | Oil* |
| Cl | CN | Oil** |
| Br | F | Oil*** |

* NMR(CDCl$_3$): 7.4(m)1H; 7.3(m)10H; 7.1(m)2H; 5.2(s)2H; 5.05(s)2H; 4.6(m)1H; 3.5–3.4(m)8H; 2.6–2.0(m)4H.

** NMR(CDCl$_3$): 8.25(s)1H; 7.6(m)2H); 7.4–7.2(m)10H); 7.1(d)1H; 6.2(d)1H(NH); 5.2(s)2H); 5.1(s)2H; 4.6(m)1H; 3.7–3.5(m)8H; 2.7–2.2(m)4H.

*** NMR: 7.4–6.8(m)13H; 5.7(d)1H; 5.2(s)2H; 5.1(s)2H; 4.6(m)1H; 3.7–3.3(m)8H; 2.6–1.9(m)4H.

EXAMPLES 25–32

The following compounds:

TABLE 14

[Structure: bis(2-chloroethyl)amino-phenyl-O-C(=O)-NH-CH(CO₂H)-Z]

| Ex No | —Z |
|---|---|
| 25 | —CH₂—CH₂—C(=O)—NH₂ |
| 26 | —CH₂—CH₂—C(=O)—NHSO₂Me |
| 27 | —CH₂—CH₂—C(=O)—NH—(3-methylphenyl) |
| 28 | —CH₂—CH₂—(1H-tetrazol-5-yl) |
| 29 | —CH₂—S—(1H-tetrazol-5-yl) |

TABLE 14-continued

[Structure: bis(2-chloroethyl)amino-phenyl-O-C(=O)-NH-CH(CO₂H)-Z]

| Ex No | —Z |
|---|---|
| 30 | —CH₂—CH₂—CO—NH—(3-CH₂CO₂H-phenyl) |
| 31 | —CH₂—CH₂—CO—NH—(3-(1H-tetrazol-5-yl)-phenyl) |
| 32 | —CH₂—CH₂—CO—NH—(3-NH₂-phenyl) | were prepared in an analogous manner to that described in Example 1 except as described hereinunder.

The NMR data for each of the compounds of Examples 25–32 is set out in the following table:

TABLE 15

| Ex No | ClCH₂CH₂N- | Aromatics | αCH | CH₂-X | Other |
|---|---|---|---|---|---|
| 25 | 3.69(m)8H | 6.7–6.9(m)4H | 3.97(m)1H | 1.79–1.99(m)2H | 2.2(t)2H<br>6.7(bs)1H<br>7.27(bs)1H<br>7.89(bs)1H |
| 26 | 3.70(s)8H | 6.70–6.93(-)4H | 4.0(m)1H | 1.85–2.2(m)2H | 2.42(m)2H<br>3.19(s)3H<br>7.90(d)1H |
| 27 | 3.71(s)8H | 6.69–7.38(m)8H | 4.04(m)1H | 1.9–2.1(m)2H | 2.45(m)2H<br>2.26(s)3H<br>7.89(d)1H<br>9.83(s)1H |
| 28 | 3.73(s)8H | 6.7–6.9(m)4H | 4.08(m)1H | 2.1–2.27(m)2H | 3.03(t)2H<br>8.03(d)1H<br>12.79(bs)1H |
| 29 | 3.69(s)8H | 6.72–6.93(m)4H | 4.38(m)1H | 3.46–3.8(m)2H | 8.12(d)1H |
| 30 | 3.70(s)8H | 6.6–7.6(m)8H | 4.05(m)1H | 1.8–2.3(m)2H | 2.45(m)2H<br>3.50(s)2H<br>7.9(d)1H<br>9.9(s)1H<br>12.5(broad s) |
| 31* | 3.67(s)8H | 6.5–8.5(m)8H | 4.10(m)1H | 1.8–2.3(m)2H | 2.5(m)2H |
| 32 | 3.70(s)8H | 6.22–7.21(m) | 4.03(m)1H | 1.8–2.2(m)2H | 2.50(m)2H<br>7.79(d)1H<br>9.52(s)1H |

*NMR run with CD₃CO₂D added

The compound of Example 25 was prepared as described in Example 1, but using α-benzyl-4-[N,N-bis(2-chloroethyl)-amino]phenoxycarbonyl-L-glutamine in the hydrogenation reaction, the preparation of which is described hereinafter. Tetrahydrofuran was added to the ethyl acetate in the hydrogenation reaction to help solubilise the above-mentioned α-benzyl compound.

The compounds of Examples 26 and 27 were prepared as described in Example 1 by hydrogenolysis of the intermediates α-benzyl 4-[N,N-bis(2-chloroethyl)amino] phenoxycarbonyl-L-mesylglutamine and α-benzyl 4-[N,N-bis(2-chloroethyl)amino]phenoxycarbonyl-L-(-3-methylphenyl)glutamine respectively.

The compound of Example 28 was prepared as described in Example 1 by hydrogenation of benzyl 4-[N,N-bis(2-chloroethyl)amino]-phenoxycarbonyl-γ-(5-tetrazolyl)-α-amino-L-butyrate. The compound of Example 28 was also prepared by a second method as set out immediately hereinafter. A process analogous to that described in Example 1 was followed but using (S)-2-amino-4-(1H-1,2,3,4-tetrazol-5-yl)butyric acid (Z. Grzonka et al. Tetrahedron, 33: 2299–2302, 1977) instead of L-glutamic acid dibenzyl ester in the reaction with O-(4-[N,N-bis(2-chloroethyl)amino]-phenyl)-O$^1$-(4-nitrophenyl)-carbonate. The reaction was carried out in dry DHF with 2 equivalents of triethylamine for 20 hours at 25° C. After evaporation to dryness, the residue was dissolved in ethyl acetate, washed with dilute citric acid, dried and evaporated to dryness. The product crystallised slowly from ethyl acetate. The residue was recrystallised from ethyl acetate to give the compound of Example 28 (m.p. 173–5° C.).

The compound of Example 29 was prepared by a procedure similar to that described for the first preparation of Example 28, but 1-{4-[N,N-bis(2-chloroethyl)amino] phenoxy-carbonylamino}-1-benzyloxy-carbonyl-2-(5-thiotetrazole)-ethane was used instead of benzyl 4-[N,N-bis(2-chloroethyl)amino]phenoxycarbonyl-γ-(5-tetra-zolyl)-α-amino-L-butyrate. A similar reaction work up gave a gum which was purified by column chromatography on silica, eluting with 4% formic acid/ethyl acetate (by volume).

The compound of Example 29 was also prepared by a second method as set out immediately hereinafter.

1-amino-1-carboxy-2-(5-thiotetrazole)ethanne (600 mg, 2.89 mM) was suspended in dry DMF (48 mls), triethylamine (0.806 mls, 578 mM) was added and the suspension stirred. O-(4-[N,N-bis(2-chloroethyl)amino]-phenyl)-O$^1$-(4-nitrophenyl)carbonate (1.10 g, 2.89 mM) was added in a single portion as a solid and the solution stirred for 20 hours at room temperature. DMF was removed in vacuo. The residue was dissolved in ethyl acetate and dilute citric acid. The ethyl acetate layer was washed with water, dried with sodium sulphate, filtered and evaporated. The crude product obtained was chromatographed on silica gel and eluted with 4% formic acid in ethyl acetate to give 4-[N-N,bis(2-chloroethyl)amino]phenoxycarbonyl amino-1-carboxy-2-(5-thiotetrazole)ethane as a glassy solid (0.963 g).

NMR (DMSOd$_6$) 3.46(dd, 1H); 3.69(s, 8H); 3.8(dd, 1H); 4.38(m, 1H); 6.72(d, 2H); 6.93 (d, 2H); 8.12 (d, 1H).

The compounds of Examples 30 and 31 were prepared as described in Example 1 by hydrogenation of α-benzyl 4-[N,N-bis(2-chloroethyl)amino]phenoxycarbonyl-γ-[3-(benzyloxycarbonyl-methyl)-phenyl]-L-glutamine and α-benzyl 4-[N,N-bis(2-chloroethyl)-amino] phenoxycarbonyl-γ[[3-(5-tetrazolyl)-phenyl]-L-glutamine respectively.

The compound of Example 32 was prepared as described in Example 1 by hydrogenation of α-benzyl-4-[N,N-bis(2-chloroethyl)-amino]phenoxycarbonyl-γ-[3-(benzyloxycarbonylamino)phenyl]-L-glutamine.

Intermediates for use in Preparing the Compounds of Examples 25–32

α-Benzyl-4-[N,N-bis(2-chloroethyl)amino] phenoxycarbonyl-L-glutamine, for use in preparing the compound of Example 25, was prepared as described in Example 1 from O-(4-[N,N-bis(2-chloroethyl)amino]-phenyl)-O'-(4-nitrophenyl)carbonate but substituting α-benzyl-L-glutamine (L. Zervas et al. J. Am. Chem. Soc 87 (1), 99–104, 1965) for L-glutamic acid dibenzyl ester tosylate. The product was purified by flash column chromatography on silica, elution being with 80% EtOAc/20% Hexane. The product was obtained as a white solid after trituration with ether.

α-Benzyl 4-[N,N-bis(2-chloroethyl)amino] phenoxycarbonyl-γ-mesyl L-glutamine, for use in the preparation of the compound of Example 26, was prepared as follows:

N-Boc-α-benzyl-L-glutamate [E. Klieger et al, Ann. 673. 196–207, 19641 (10 g) in 50 ml dry dichloromethane was treated with dimethylaminopyridine (DMAP)(3.9 g) and dicyclohexylcarbodiimide (6.73 g). Methane sulphonamide (3.04 g) was then introduced to the reaction flask and the reaction continued at 25° C. for 20 hrs. Dichloromethane was evaporated and the residue redissolved in ethyl acetate. Ethyl acetate solution was then washed with 0.25M citric acid, followed by water and then dried over Na$_2$SO$_4$ (anhydrous). Evaporation of the ethyl acetate extract gave a residue which was purified on silica using flash column chromatography using as eluent methylene chloride, then 5% methanol/methylene chloride and then 10% methanol/methylene chloride to give the Boc-protected acyl sulphonamide:

(L)

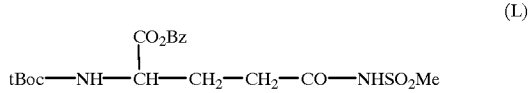

NMR: δ 1.37(s)9H; 1.98(m)2H; 2.34(t)2H; 5.11(d)2H; 7.26(d)1H; 7.36(s)5H; 11.64(s)1H.

3.6 g of the Boc-protected acyl sulphonamide was suspended in 50 ml ethyl acetate followed by the addition of 8 equivalents of HCl saturated ethyl acetate (22.4 ml of 3.1H solution). The starting material sulphonamide went into solution and the reaction was allowed to continue for 20 hrs, under argon, at 25° C. α-Benzyl γ-mesyl-L-glutamine hydrochloride of the formula:

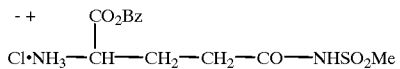

was produced as a white solid which was filtered off and washed with anhydrous ether before drying in a dessicator. NMR: δ2.08(m)2H; 2.52(m)2H; 3.20(s)3H; 4.09(t)1H; 5.15–5.35(dd)2H, 7.39–7.50(m)5H, about 9 (broad) 3H.

α-Benzyl 4-[N,N-bis(2-chloroethyl)amino] phenoxycarbonyl-L-mesylglutamine was prepared as described in Example 1 from O-(4-N,N-bis(2-chloroethyl) amino]-phenyl)-O'-(4-nitrophenyl)carbonate but substituting α-benzyl γ-mesyl-L-glutamine hydrochloride for L-glutamic acid dibenzyl ester tosylate. The product of the reaction was purified by column chromatography on silica, eluting with 10% formic acid in ethyl acetate (by volume).

α-Benzyl 4-(N,N-bis(2-chloroethyl)amino]-phenoxycarbonyl-γ-(3-methylphenyl)-L-glutamine, for use in the preparation of the compound of Example 27 was prepared as follows:

α-Benzyl 4-[N,N-bis(2-chloroethyl)amino] phenoxycarbonyl-L-glutamate was prepared as described in Example 1 from O-(4-[N,N-bis(2-chloroethylamino]-phenyl)-O'-(4-nitrophenyl)carbonate but substituting α-benzyl-L-glutamate (Ref. C. Coutsogeorgopaulos et al J. Am. Chem. Soc. 83, 1885, 1961) for L-glutamic acid dibenzyl ester. Moreover the reaction was performed in dry DMF at 25° C. for 2 hrs. The product was purified by column chromatography (silica, Merck Art 9385) using ethyl acetate/hexane mixtures in the range 70/30 respectively to 100% ethyl acetate. The NMR data for the product is set out in Table 17.

α-Benzyl 4-[N,N-bis(2-chloroethyl)amino] phenoxycarbonyl-L-glutamate (300 mg) in dry tetrahydrofuran (5 ml) was treated with 1.1 equivalents of triethylamine. Isobutylchloroformate (0.08 ml, 1.1 equiv) in dry THF (10 ml) was added slowly to the reaction mixture at −25° C. After 15 minutes, 1.1 equivalents (0.08 ml) m-toluidine in dry tetrahydrofuran (5 ml) was added. The mixture was allowed to warm up to 25° C. and was then continuously stirred for 18 hrs. The reaction mixture was then filtered and the filtrate evaporated to give a residue which was purified by flash column chromatography using mixtures of ethyl acetate/hexane as eluent. Evaporation of appropriate fractions yielded α-benzyl 4-[N,N-bis(2-chloroethyl)-amino]phenoxycarbonyl-γ-(3-methylphenyl)-L-glutamine as a white crystalline solid. The NMR data from this product is set out in Table 17.

1-{4-[N,N-bis(2-chloroethyl)amino] phenoxycarbonylamino}-1-benzyloxycarbonyl-2-(5-thiotetrazole)-ethane for use in the prepartion of the compound of Example 29 was prepared as follows:

1-amino-1-carboxy-2-(5-thiotetrazole)ethane was prepared by adding β-chloroalanine (18.50 g, 115.6 mmol) (Sigma Chemical Co) and 5-thiotetrazole (11.79 g, 115.6 mmol (prepared as described in European Patent Publication No. 33965) to 230 mls of a 2M sodium hydroxide solution with stirring. The reaction mixture was then heated from room temperature to 90° C. for 1½ hours. The reaction mixture was then allowed to cool to room temperature and then cooled further with ice/methanol bath cooling, the mixture was acidified to pH4.0 with concentrated hydrochloric acid and stirring was maintained for ½ hour. The resulting precipitate was filtered off, washed with cold water and then with ether and filtered dry with suction to give 6.9 g. The mother liquor's pH was re-checked and found to have risen to about 5.5. The above procedure was repeated and a further 2.3 g of product obtained. This was dried under high vacuum.

NMR: δ 3.30–3.50 ppm(m)2H; 4.16–4.22 ppm(q)1H; 7.47 ppm (broad) $H_2O$ exchanging with $NH_2$.

Elemental Analysis

Expected C=23.2, H=4.4; N=33.8 (+1 mol of $H_2O$)

Found C=23.1; H=4.4; N=33.7 (9.6% $H_2O$).

1-{4-[N,N-bis(2-chloroethyl)amino] phenoxycarbonylamino}-1-benzyloxycarbonyl-2-(5-thiotetrazole)-ethane was prepared as described in Example 1 from O-(4-[N,N-bis(2-chloroethyl)amino]-phenyl)-O'-(4-nitrophenyl)carbonate, but substituting γ-(5-thiotetrazolyl)-α-benzyloxycarbonyl-amino-L-butyric acid (Ref. Z Grzonka et al Tetrahedron Letters 33 2399–2302, 1977) for L-glutamic acid di-benzyl ester. Dry dimethylformamide was used as solvent and the reaction was carried out at 25° C. The reaction mixture worked up after 2 hours and the product purified by flash column chromatography on silica and eluting with a mixture made up of 2% formic acid in ethyl acetate/methylene chloride (3:1 by volume). The NMR data for this product is set out in Table 16.

α-Benzyl 4-[N,N-bis(2-chloroethyl)amino]-phenoxycarbonyl-γ-[3-(benzyloxycarbonylmethyl)phenyl]-L-glutamine, for use in Example 27 was prepared as follows:

3-amino-phenylacetic acid benzyl ester p-toluene sulphonic acid was prepared by adding 3-aminophenylacetic acid (10 g) and p-toluene sulphonic acid monohydrate (13.2 g) to benzyl alcohol (27.2 ml) in toluene (30 ml). The mixture was heated under reflux and the water formed collected in a Dean-Stark receiver. When all the water had been distilled off the mixture was allowed to cool to 25° C. before diluting with diethyl ether and placing in an ice-bath for 1 hr. The crystalline p-toluene sulphonate was filtered off and dried in a dissicator (23.5 g) NMR δ 2.31(s)3H, 3.82(s)2H, 5.11(s)2H, 7.11(d)2H, 7.25–7.45(m)8H, 7.52(d)2H.

α-Benzyl 4-[N,N-bis(2-chloroethyl)amino] phenoxycarbonyl-γ-[3-(benzyloxycarbonylmethyl)phenyl]-L-glutamine was prepared as described in Example 27 but substituting 3-aminophenylacetic acid benzyl ester for m-toluidine.

α-Benzyl 4-[N,N-bis(2-chloroethyl)amino]phenoxy-carbonyl-γ-[3-(5-tetrazolyl)phenyl]-L-glutamine, for use in Example 31 was prepared as described in Example 27, but substituting 3-(tetrazol-5-yl)-aniline for m-toluidine. The 3-(tetrazol-5-yl)-aniline required as a starting material was prepared as follows. To a solution of 5-(3-nitrophenyl) tetrazole (Finnegan W. G.; Henry R. A., and Lolquist R. J.A.C.S. 80:3908 (1958)) (52 g) in ethanol (2.51) was added 10% palladium on carbon (5 g) and the mixture stirred under an atmosphere of hydrogen for 16 h. The catalyst was removed by filtration and the filtrate evaporated to give the desired starting material (40.5 g; m.p.=188–9° C.).

α-Benzyl-4-[N,N-bis(2-chloroethyl)amino] phenoxycarbonyl-γ-[3-(benzyloxycarbonylamino)phenyl]-L-glutamine for use in Example 32 was prepared as described in Example 27 but substituting 3-(benzoyloxy-carbonylamino)aniline for m-toluidine.

NMR $ClCH_2CH_2N$: 3.68(m)8H;

Aromatics: 6.68–7.74(m)1H;

$ArCH_2O$: 5.12(s)2H; 5.14(s)2H;

αCH: 4.18(m)1H;

Other: 1.9–2.15(m)2H; 2.45(m)2H; 8.12(d)1H; 9.7(s)1H; 9.9(s)1H.

3-(benzoyloxycarbonylamino)aniline used as an intermediate in preparation of Example 32, was prepared as follows. To a cold solution (0°) of m-phenylene diamine (10 g) in ethyl acetate (200 ml) was added aq $KHCO_3$ (9 g in 300 ml water) with stirring. Benzyl chloroformate (13.2 ml) in ethyl acetate (100 ml) was added dropwise over ten minutes, stirred at 0° C. for one hour and then made acid (pH2) by addtion of M.HCl (aq). The product was extracted into ethyl acetate (250 ml), washed with brine, dried over $MgSO_4$ and reduced in "vacuo" to give an oil. The oil was chromatographed on Merck silica gel Art 9385 and eluted with hexane/ethyl acetate (7:3) to give 8 g of the intermediate as a low melting point solid (36% yield).

NMR: 9.32(s)1H; 7.30(m)5H; 6.80(t)1H; 6.70(m)1H; 6.50(m)1H; 6.12(m)1H; 5.0(s)2H; 4.88(s)2H.

TABLE 16

| X | ClCH$_2$CH$_2$N- | Aromatics | ArCH$_2$O | α CH | CH$_2$-X | Other |
|---|---|---|---|---|---|---|
| CH$_2$CO$_2$H | 3.63(m)8H | 6.62–7.31(m)9H | 5.11(s)2H | 4.14(m)1H | 1.8–2.05(m)2H | 7.89(d)1H<br>2.35(m)2H |
| CH$_2$CONH$_2$ | 3.71(m)8H | 6.7–7.3(m)9H | 5.15(s)2H | 4.13(m)1H | 1.8–2.03(m)2H | 2.23(t)2H<br>6.77(s)1H<br>7.28(s)1H<br>8.08(d)1H |
| CH$_2$CONHSO$_2$Me | 3.71(m)8H | 6.7–7.37(m)9H | 5.15(s)2H | 4.15(m)1H | 1.8–2.1(m)2H | 2.49(m)2H<br>3.19(s)3H<br>11.7(bs)1H<br>8.1(d)1H |
| CH$_2$CONH- | 3.71(m)8H | 6.69–7.42(m)13H | 5.18(s)LH | 4.19(m)1H | 1.9–2.2(m)2H | 2.49(m)2H<br>2.25(s)3H<br>8.11(d)1H<br>9.83(s)1H |
| CH$_2$- | 3.71(m)8H | 6.7–7.37(m)9H | 5.17(s)2H | 4.23(m)1H | 2.1–2.3(m)2H | 8.23(m)2H<br>3.03(t)2H |
| CH$_2$CONH- | 3.70(m)8H | 6.6–7.6(m)18H | 5.10(s)2H<br>5.17(s)2H | 4.19(m)1H | 1.9–2.3(m)2H | 2.45(m)2H<br>3.67(s)2H<br>8.13(d)1H<br>9.90(s)1H |
| CH$_2$CONH- | 3.70(s)8H | 6.6–8.5(m)13H | 5.15(s)2H | 4.2(m)1H | 1.9–2.3(m)2H | 2.15(m)2H<br>8.15(d)1H<br>10.2(s)1H |

EXAMPLE 33

N-(4-[N,N-bis(2-iodoethyl)amino]phenoxy-carbonyl)-L-glutamic Acid

4-[N,N-bis(2-iodoethyl)amino]phenoxy-carbonyl-L-glutamic acid di-t-butyl ester (188 mg) (See Scheme 9—Compound 14) was suspended in trifluoroacetic acid (TFA) (4 ml) and stirred for 30 min at ambient temperature. TFA was removed under reduced pressure; the remaining oil was diluted with ethyl acetate (3 ml) and evaporated to give 4-[N,N-bis(2-iodoethyl)amino]phenoxycarbonyl-L-glutamic acid-1.4 TFA-0.8 EtOAc (162 mg) 82% yield; (Compound 15 in Scheme 9). NMR: 1.84–2.01 (m) 1H; 2.36 (m) 2H; 3.31 (t) 4H; 3.72 (t) 4H; 4.02 (m) 1H 6.66 (d) 2H; 6.94 (d) 2H; 7.92 (d) 1H.

4-[N,N-bis(2-iodoethyl)amino]phenoxy-carbonyl-L-glutamic acid di-t-butyl ester used as intermediate was prepared as follows:

a) A solution of the product bis(2-mesyloxyethyl)amino]-phenoxycarbonyl-L-glutamic acid di-t-butyl ester (1.0 g) (See Scheme 9—compound 11) in acetonitrile (50 ml) was stirred with sodium iodide (1.0 g) at 70° C. for 20 h. The reaction mixture was filtered and the filtrate concentrated under vacuum. The residue was chromatographed on silica gel; eluted with ethyl acetate in cyclohexane (1:5) to obtain 4-[N,N-bis(2-iodoethyl)amino]phenoxycarbonyl-L-glutamic acid di-t-butyl ester (see Scheme 9—Compound 14) as an oil (0.75 g) 68% yield. NMR: 1.41 (s) 9H; 1.43 (s) 9H; 1.81–1.95 (m) 1H; 2.34 (m) 2H; 3.31 (t) 4H; 3.72 (t) 4H; 4.00 (m) 1H; 6.67 (d) 2H; 6.93 (d) 2H; 7.91 (d) 1H.

b) bis(2-mesyloxyethyl)amino]phenoxycarbonyl-L-glutamic acid di-t-butyl ester

A solution of 4-[N,N-bis(2-hydroxyethyl)amino]-phenoxycarbonyl-L-glutamic acid di-t-butyl ester (2.53 g) (obtained as described in Example 8—see also Scheme 4) in pyridine (9 ml) was stirred with methanesulphonyl chloride (1.8 ml) at 2° C. for 20 min followed by 80° C. for 11 min. The reaction mixture was partitioned between ethyl acetate and citric acid/water (10%). The organic phase was separated, washed with water, dried (Na$_2$SO$_4$) and evaporated to dryness. The residue was chromatographed on silica gel; eluted with ethyl acetate in dichloromethane (1:9) to obtain 4-[N,N-bis(2-mesyloxyethyl)amino]phenoxycarbonyl-L-glutamic acid di-t-butyl ester (Compound 11 in Scheme 9) as an oil (0.95 g) 28% yield. NMR: 1.41 (s) 9H; 1.43 (s) 9H; 1.8–1.99 (m) 1H; 2.34 (m) 2H; 3.16 (s) 6H; 3.72 (t) 4H; 3.9 (m) 1H; 4.31 (t) 4H; 6.78 (d) 2H; 6.92 (d) 2H; 7.9 (d) 1H.

EXAMPLE 34

N-(4-[N,N-bis(2-bromoethyl)amino]phenoxy-carbonyl)-L-glutamic Acid

4-[N,N-bis(2-bromoethyl)amino]phenoxy-carbonyl-L-glutamic acid di-t-butyl ester (133 mg) [see Scheme 9—compound (12)] was suspended in TFA (4 ml) and stirred for 30 min at ambient temperature. TFA was removed under reduced pressure; the remaining oil was diluted with ethyl acetate (3 ml) and evaporated to give 4-[N,N-bis(2-bromoethyl)amino]phenoxy-carbonyl-L-glutamic acid-1.3 TFA-0.9 EtOAc (126 mg) 80% yield. [see Scheme 9—compound (13)]. NMR: 1.83–2.01 (m) 1H; 2.36 (m) 2H; 3.58 (t) 4H; 3.76 (t) 4H; 4.03 (m) 1H; 6.71 (d) 2H; 6.94 (d) 2H; 7.92 (d) 1H.

4-[N,N-bis(2-bromoethyl)amino]phenoxy-carbonyl-L-glutamic acid di-t-butyl ester used as intermediate was prepared as follows:

A solution of bis(2-mesyloxyethyl)amino]phenoxy-carbonyl-L-glutamic acid di-t-butyl ester (0.48 g) (compound 11 in Scheme 9—obtained as described in Example 8—see also Scheme 4) in acetonitrile (30 ml) was stirred with lithium bromide (0.26 g) at 70° C. for 22 h. The reaction mixture was filtered and the filtrate concentrated under vacuum. The residue was chromatographedon silica gel; eluted with ethyl acetate in dichloromethane (1:5) to obtain 4-[N,N-bis(2-bromoethyl)amino]phenoxycarbonyl-L-glutamic acid di-t-butyl ester (compound 12 in Scheme 9) as an oil (0.37 g) 83% yield. NMR: 1.41 (s) 9H; 1.43 (s) 9H; 1.8–1.98 (m) 1H; 2.34 (m) 2H; 3.58 (t) 4H; 3.76 (t) 4H; 3.97 (m) 1H; 6.72 (d) 2H; 6.93 (d) 2H; 7.93 (d) 1H.

EXAMPLE 35

N-(4-[N,N-bis-(2-chloroethyl)amino]2-fluoro-phenylcarbamoyl)-L-glutamate

The titled compound (NMR (dmso): 8.0(s) 1H; 7.65(t) 1H; 6.6(m) 3H; 4.2(m) 3H; 3.7(s)8H; 2.28(m)2H; 1.8(m)

2H) was prepared from the intermediate dibenzyl 4-[N,N-bis(2-chloroethyl)amino]2-fluoro-phenylcarbamoyl-L-glutamate (NMR (dmso): 7.62(t)1H; 7.35(s)10H; 6.8(d)1H; 6.57(m)2H; 5.1(d)4H; 4.33(m)1H; 3.7(s)8H; 2.43(m)2H, 2.0(m)2H) in a manner analogous to the corresponding step of Example 5.

The intermediate was prepared as follows:

Ethylene oxide (6.6 g) was added to 3-fluoro-4-nitroaniline (1.3 g) in glacial acetic acid (30 ml) and the reaction mixture was kept in a closed flask at laboratory temperature for 72 h. The solution was evaporated under reduced pressure to half of its original volume, diluted with saturated aqueous sodium chloride solution and extracted three times with ethyl acetate. The ethyl acetate extracts were combined, washed with saturated aqueous sodium bicarbonate, evaporated, and the residue was purified by flash column chromatography on silica gel. After elution with hexane containing 50% (v/v) ethyl acetate to remove unchanged starting material and monosubstituted product. Elution with ethyl acetate gave the product 2',2'-(3-fluoro-4-nitroanilino)diethanol (m.pt. 99–101° C.).

The product so obtained (280 mg) was dissolved in dichloromethane (7.5 ml), pyridine (0.1 ml) was added and the solution was cooled in an ice/water bath. Thionyl chloride (0.25 ml) was added dropwise, with stirring. When the addition was complete the reaction mixture was heated under reflux for 1 hour and then left at, laboratory temperature for 20 hours. The solution was diluted with dichloromethane (10 ml) and washed three times with water, dried over sodium sulphate, evaporated, and the residue was recrystallised from methanol to give the product [N,N-bis(2-chloroethyl]-3-fluoro- 4-nitroaniline (mp 97–98° C.).

The product so ob tained (200 mg) in tatrahydrofuran (7.5 ml) was stirred for 16 hours in an atmosphere of hydrogen in the presence of palladium/charcoal (20 mg of 5% w/w). The catalyst was removed by filtration and the solvent was evaporated. The resulting residue was dissolved in the minimum volume of methanol and the crude product was precipitated by addition of excess diethyl ether saturatd with hydrogen chloride. Recrystallisation from methanol/diethyl ether gave the product 4-[N,N-bis(2-chloroethyl)amino-2-fluoro-anilinium choride (m.pt. 195–200° C.,d).

The resulting product was converted into the desired intermediate in a manner analogous to the corresponding step in Example 5.

EXAMPLES 36–43

The structures and elemental analysis data for compounds of Examples 36–43 are set out in Table 17.

The compounds listed in Table 17 were prepared according to the procedures described in Example 16. Thus the compound of example 36 was prepared by substituting benzyl-4-aminobenzoate (Aldrich Chemical Co Ltd) for aniline in Example 16. Simiarly, the compounds of examples 37–43 were prepared by substituting benzyl 4-aminobenzoate, sec-butylamine, n-propylamine, isopropylamine, cyclohexylamine, benzylamine or p-benzyloxyaniline for aniline in Example 16.

TABLE 17

$$\text{ClCH}_2\text{CH}_2\diagdown\text{N}-\!\!\left\langle\!\!\!\bigcirc\!\!\!\right\rangle\!\!-\text{OCONHCH}\!\!\begin{array}{c}\text{COOH}\\|\\\text{CH}_2\text{CH}_2\text{W}\end{array}$$
$$\text{ClCH}_2\text{CH}_2\diagup$$

| Ex. No. | W | % Expected | | | % Found | | |
|---|---|---|---|---|---|---|---|
| | | C | H | N | C | H | N |
| 36 | —CO—NH-p-$C_6H_5$COOH | 51.5 | 5.26 | 7.83 | 51.7 | 5.10 | 7.50 |
| 37 | —CO—NH-n-$C_4H_9$ | 51.9 | 6.32 | 9.09 | 52.0 | 6.38 | 8.97 |
| 38 | —CO—NH-sec-$C_4H_9$ | 51.9 | 6.32 | 9.09 | 52.2 | 6.34 | 9.09 |
| 39 | —CO—NH-n-$C_3H_7$ | 50.9 | 6.07 | 9.37 | 50.6 | 6.35 | 8.95 |
| 40 | —CO—NH-i-$C_3H_7$ | 50.9 | 6.07 | 9.37 | 51.1 | 6.07 | 9.40 |
| 41 | —CO—NH—$C_6H_{11}$ | 54.1 | 6.40 | 8.60 | 54.3 | 6.73 | 8.72 |
| 42 | —CO—HN—$CH_2C_6H_5$ | 55.6 | 5.48 | 8.46 | 56.0 | 5.52 | 8.21 |
| 43 | —CO—NH-p-$C_6H_5$OH | 53.0 | 5.06 | 8.43 | 53.0 | 5.24 | 7.90 |

EXAMPLE 44

N-(4-N,N-bis(2-chloroethyl)amino]phenylcarbamoyl)-L-glutamic Acid

A solution of the intermediate dibenzyl 4-[N,N-bis(2-chloro-ethyl)amino]-phenylcarbamoyl-L-glutamate (1.138 g) in DMF (15 ml) was hydrogenated over 10% Pd/C for 16 hours. After filtration and evaporation in vacuo, the residue was dissolved in $CHCl_3$ (20 ml). After 18 hours the crystalline precipitate was filtered off and dried in vacuo to obtain 4-[N,N-bis-(2-chloroethyl)amino]phenylcarbamoyl-L-glutamic acid. Yield, 730 mg (93%). After recrystallisation from acetone/$CHCl_3$ microscopic rods formed m.p. 116–118° C. NMR ($CD_3COCD_3$): δ 8.0(s)1H; 7.2(d)2H; 6.6(d)2H; 6.2(d)2H NH; 4.4(m)1H; 3.6(m)8H; 2.5–1.9(m) 4H.

The dibenzyl intermediate was prepared as follows (see Scheme 10).

Dibenzyl glutamate p-tolunesulphonate (available Bachem U.K.; 0.25 g) was dissolved in dry methylene chloride (10 ml) under argon and cooled to 0° C. Pyridine (0.162 ml) was added, followed rapidly by phosgene in toluene (1.93M, 0.311 ml). The solution was stirred at 0° C. for 2 hours, pyridine (0.05 ml) added and followed by 4-[N,N-bis (chloroethyl)amino]anilinium chloride in one portion. The mixture was stirred for 10 minutes at 0° C. and then for 18 hours at room temperature. The reaction mixture was then diluted with ethyl acetate and water. The organic layer was then washed in turn with dilute citric acid (2x), water and saturated brine; dried and evaporated to give the desired dibenzyl intermediate as a solid.

An alternative route to the dibenzyl intermediate is as follows:

To a solution of triphosgene (1 g) in chloroform (80 ml) was added at 10° C. 4-[N,N-bis-(2-chloroethyl)amino] anilinium chloride (2.7 g). Whilst keeping the tempeature at 10° C., triethylamine (4.15 ml) was added and the mixture was stirred and allowed to warm to ambient temperature for 15 minutes. To this mixture was added in one portion dibenzyl glutamate tosylate and triethylamine (1.7 ml). After 1.5 hours at ambient tempeature the mixture was diluted with chloroform (100 ml), washed twice with water, dried and evaporated to dryness. The resdiue was chromatographed on Merck silica gell Art 9385, eluting with ethyl acetate hexane to give dibenzyl 4[N,N-bis(2-chloroethyl)-amino]-phenylcarbamoyl-L-glutamate (2.5 g). m.p. 119–22° C.

EXAMPLE 45

4-[N,N-bis(2-chloroethyl)amino]phenylcarbamoyl-γ-[N(3-carboxymethyl)anilino]-L-glutamate (compound 7 in Scheme 11)

The titled compound was prepared as follows (see scheme 11). A solution of the intermediate (compound 6 in Scheme 11; 1 g) in 20 ml THF was hydrogenated over 30% d/c (100 mg) for 4 hours. The mixture was then filtered through celite and evaporated to yield a brown oil which was then purified by flash column chromatography using 1% and 3% formic acid/ethylacetate mixtures as eluent, evaporation of appropriate fractions and interaction with ether yielded 300 mg of the titled compound. NMR: $ClCH_2CH_2N$: 3.66(s)8H; Aromatics: 6.66–7.46(m)8H; αCH:4.22(m)1H; Other: 1.66–2.06(m)2H); 2.39(m)2H); 3.49(s)2H; 6.29(d)1H; 8.33(s)1H; 9.93(s)lH; 12.5(b.s)2H.

The intermediate was prepared as follows:
(a) 3-amino-phenylacetic acid benzyl ester p-toluene sulphonic acid was prepared by adding 3-aminophenylacetic acid (10 g) p-toluene sulphonic acid monohydrate (13.2 g) to benzyl alchohol (27.2 ml) in toluene (30 ml). The mixture was heated under reflux and the water formed collected in a Dean-Stark receiver. When all the water had been distilled off the mixture was allowed to cool to 25° C., before diluting with diethyl ether and placing in an ice-bath for 1 hour. The crystalline p-toluene sulphonate was filtered off and the product dried in a dessicator (23.5 g) NRM δ 2.31(s)3H, 3.82(s)2H, 5.11(s)2H, 7.11(d)2H, 7.25–7.45(m)8H, 7.52(d)2H.
(b) N Boc α benzyl L glutamate, (5 g) in 20 ml) dry DHF at 5° C. was heated with (1.1 eq; 2.45 g) hydroxybenzothiazole (HOBT) and the reaction mixture stirred at this temperature under argon for 10 minutes. (DCCI) Dicyclohexylcarbodimide (1.1 eq; 3.37 g) was then added and the reaction stirred for a further 10 minutes at 5° C. before allowing to warm to 25° C. and stirring for a further 45 minutes. 3 amino phenylacetic acid benzyl ester p-toluene sulphonic acid (the product obtained in (a)) (1.1 eq; 6 g) together with 1.1 eq triethylamine (2.23 ml) in 10 ml dry DMF was then added and the reaction mixture stirred at 25° C. for a further 20 hours. The precipitate of dicyclohexylurea was then filtered off, and the DHF filtrates evaporated to dryness. The residue was then redissolved in EtOAc. The ethyl acetate solution was then washed with $NaHCO_3(aq)$, then brine and then dried over $Na_2SO_4$ (anhydrous). Evaporation of the ethylacetate extract gave a residue which was then purified by flash column chromatography using 30,40 and 50% EtoAc/hexane mixtures as eluent. Evaporation of appropriate fractions yielded 5 g of prudct (compound 4 in scheme 11).

NMR Data: 1.39(s)9H; 1.81–2.10(m)2H; 2.38(m)2H; 3.69(s)8H; 4.03(m)1H; 5.12(m)4H; 6.92(d)1H; 7.21(m)1H; 7.35(m)11H; 7.42(d)1H; 7.52(9)1H 9.89(s)1H.

(c) The product obtained in (b) (5 g) was suspended in 10 ml ether and 5 ml dichloromethane added (to aid solubility) followed by 8 eq of saturated etheral/HCl. The reaction mixture was then allowed to stir for 20 hours at 25° C. The product was at this stage an immiscible oil. The ether was then evaporated and the residue azeotroped twice with toluene before adding ether and evaporating down to yield 5 g of product (compound 5 in scheme 11) as a yellow foam.

NMR Data $CDCl_3$: δ2.35(m)2H; δ2.65(m)2H; δ3.50(s)2H; δ4.22(bs)1H; δ5.01(s)2H; δ6.8–7.6(m)14H; δ8.65(bs)3H; δ9.35(s)1H.

(d) 1.1 eq (0.66 g) of 1.1 carbonyldiimidazole in 20 ml dry THF at 5° C. was treated with a solution containing 1 g of 4[N.N bis (2-chloroethyl)amino]anilinium chloride. The reaction mixture was then stirred at 5° C. for 15 minutes before adding 1 eq (1.84 g) of the product obtained in (c) with 1.1 eq (0.56 ml) triethylamine in 10 ml dry THF, and stirred for a further 2 hours at 25° C. The triethylamine hydrochloride ppt was then removed by filtration and the THF filtrates evaporated and the residue redissolved in EtoAc. The ethyl acetate solution was then washed with water, followed by 0.25 M citric acid, then brine and dried over $Na_2SO_4$ (anhydrous). Evaporation of the ethyl acetate gave a residue which was purified by flash column chromatography using 30,40 and 50% ethylacetate/hexane mixture as eluent. Evaporation of appropriate fractions yielded the desired intermediate (compound 6 in scheme 11).

NMR Data: $ClCH_2CH_2N$: 365 (s)8H; Aromatics: 6.63–7.5(m)18H; $ArCH_2O$: 5.10(s)2H; 5.12(s)2H; αCH; 4.32(m)1H; Other: 1.83–2.13(m)2H; 2.41(m)2H; 6.42(d)1H; 8.25(s)1H; 9.91(s)1H.

EXAMPLE 46

4-[N,N-bis(2-chloroethyl)amino]phenoxycarbonyl-L-glutamic Acid-γ-(3,5-dicarboxy)anilide The process described in Example 16 was repeated using α-benzyl 4-[N,N-bis(2-chloroethyl)amino] phenoxycarbonyl-L-glutamic acid-γ-(3,5-dicarboxybenzyl) anilide in place of α-benzyl 4-(N,N-bis(2-chloroethyl) amino]phenoxycarbonyl-L-glutamic acid-γ-anilide to obtain 4-[N,N-bis(2-chloroethyl)amino]phenoxy-carbonyl-L-glutamic acid-γ-(3,5-dicarboxy) anilide as colourless crystals (m.p. 167–170° C.).

Elemental analysis:

% expected C=49.6 H=4.87 N=6.68

% found C=49.7 H=4.9 N=6.7.

The α-benzyl 4-benzyl 4-[N,N-bis(2-chloroethyl)amino]-phenoxycarbonyl-L-glutamic acid-γ-(3,5-dicarboxybenzyl) anilide was obtained in an analogous manner to that described in Example 16 for the γ-anilino derivative.

SCHEME 1
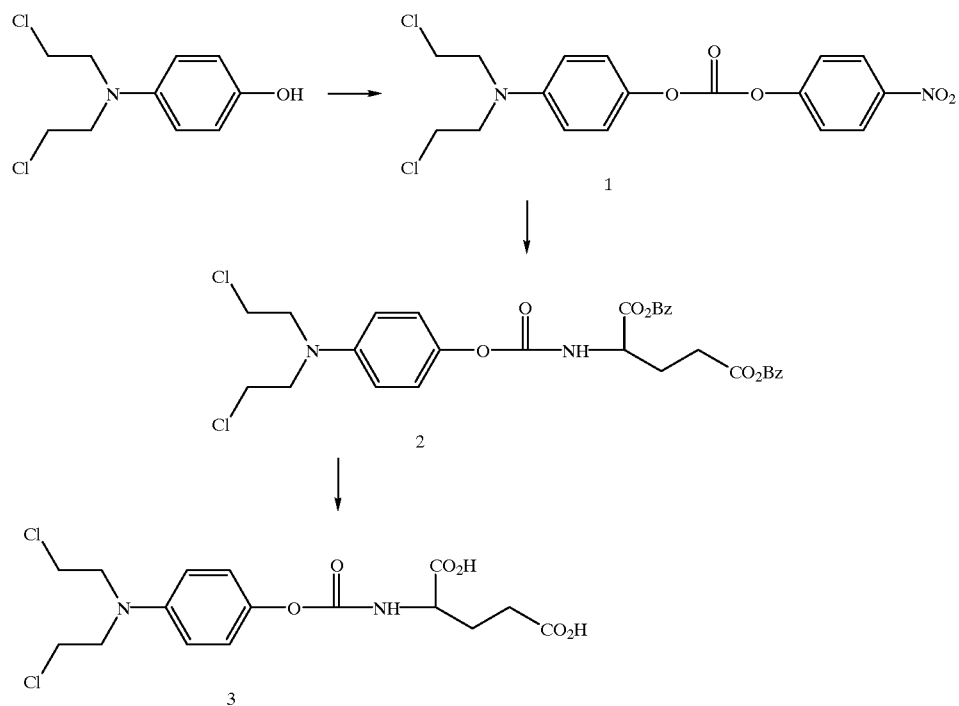
SCHEME 2
SCHEME 3
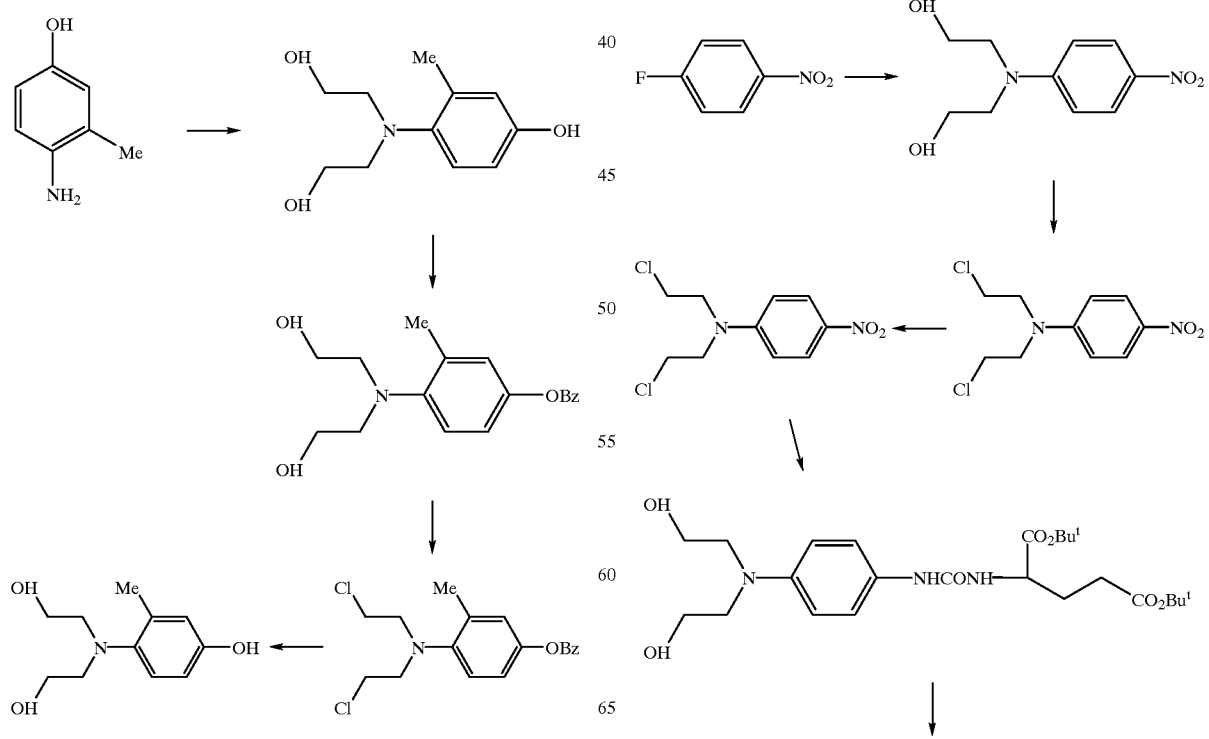

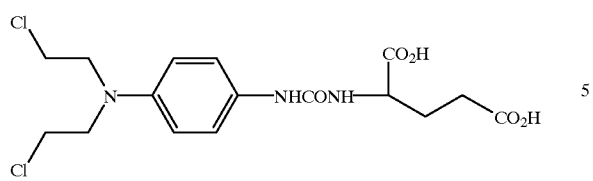
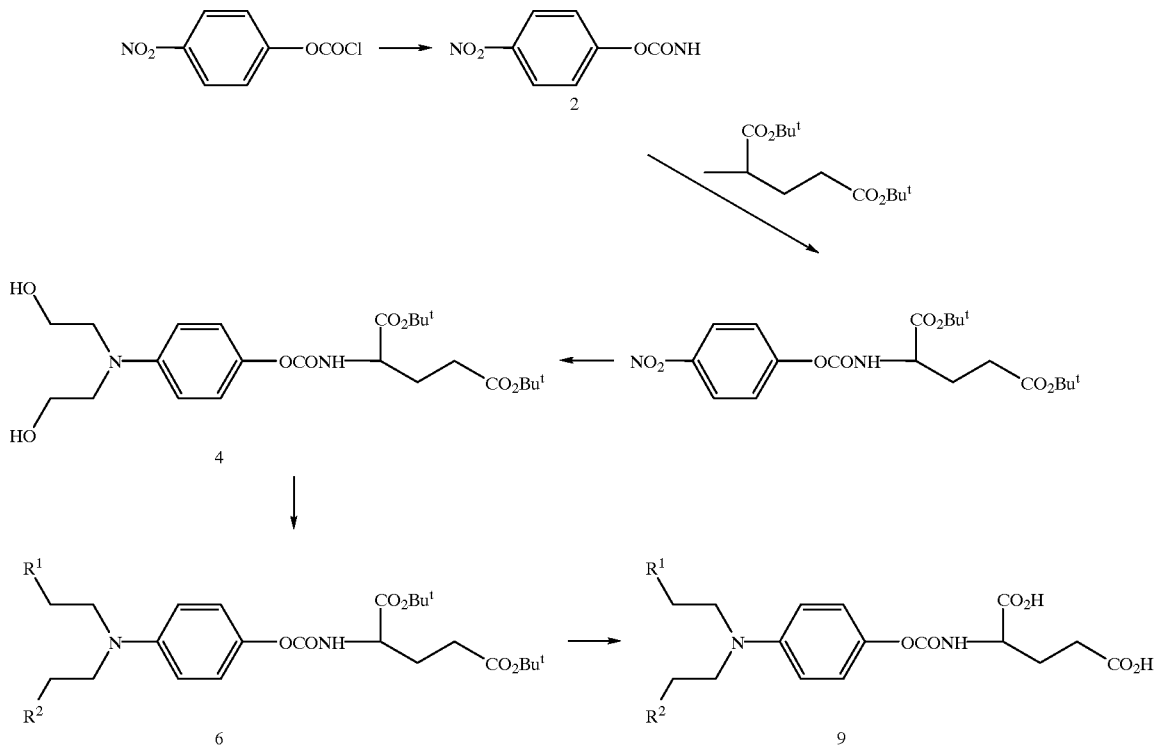
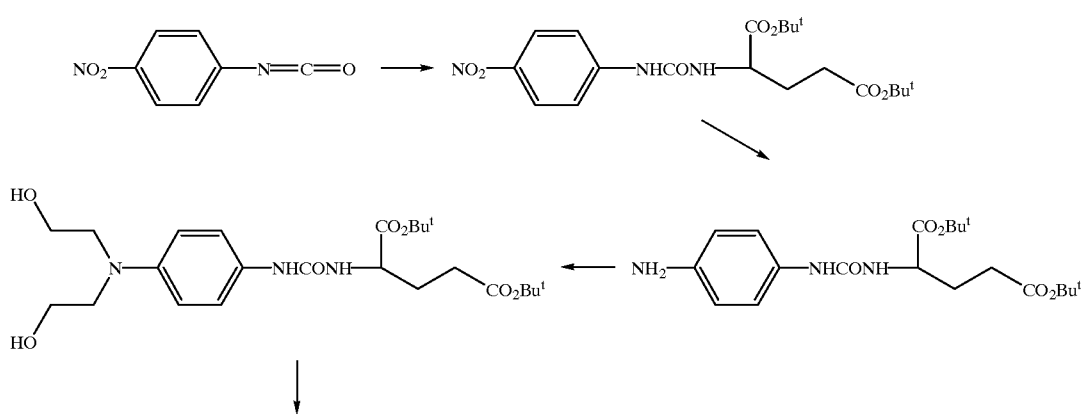

51 52
-continued
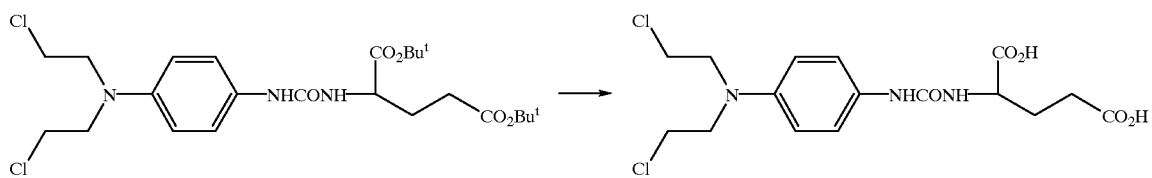
SCHEME 6
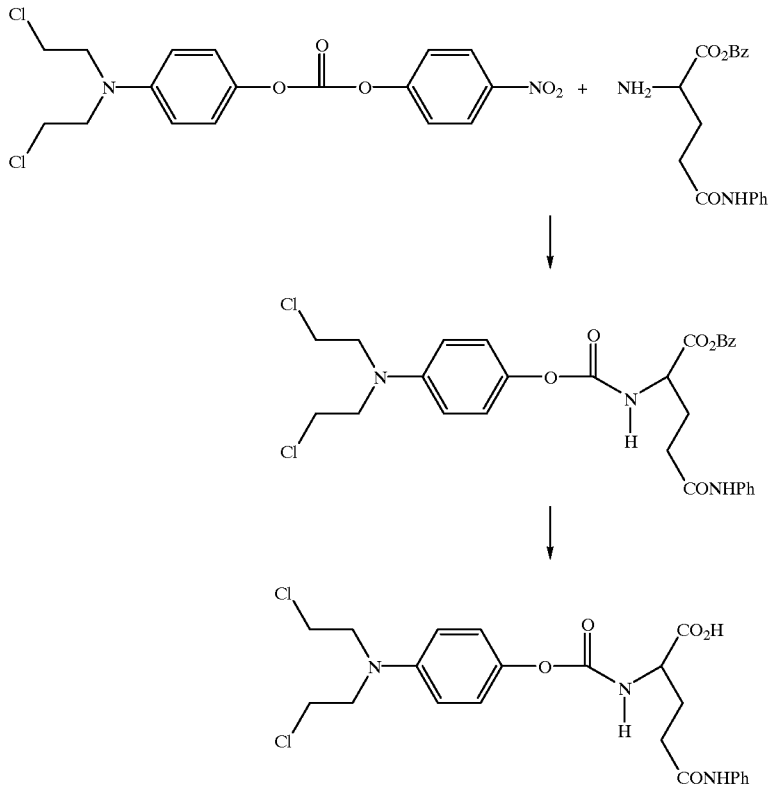
SCHEME 7
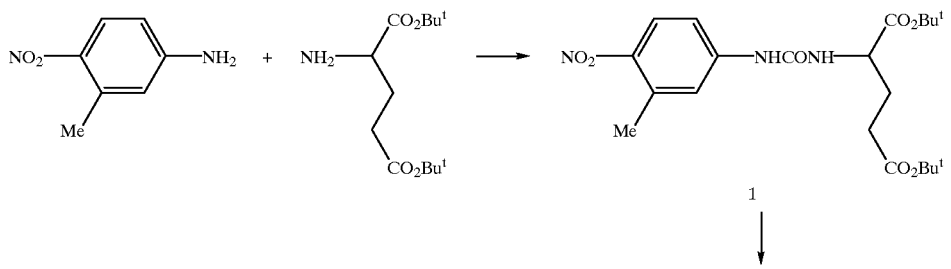

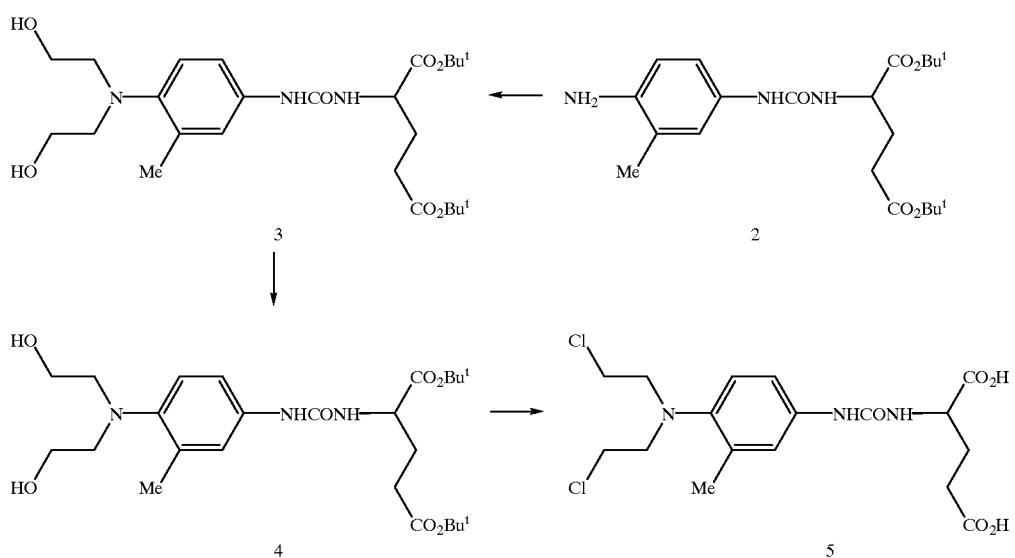
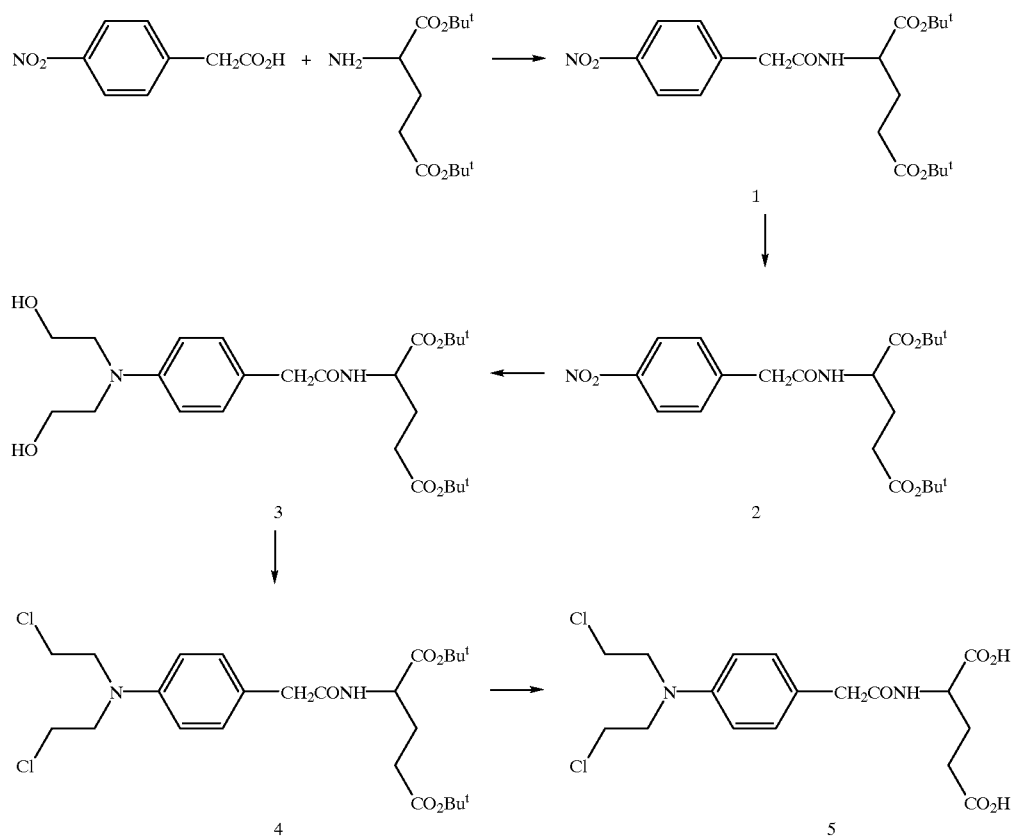
SCHEME 8

SCHEME 9
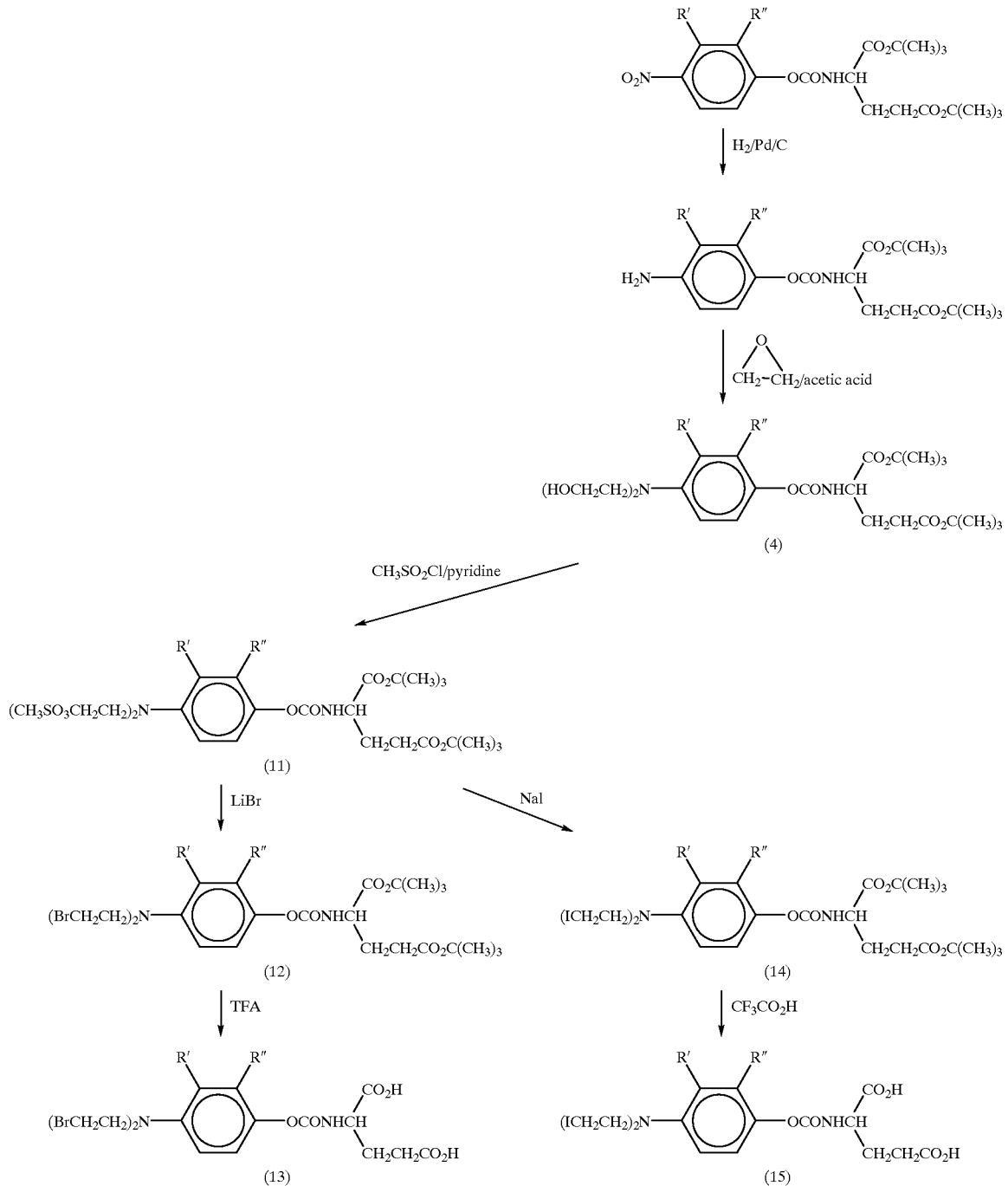

Scheme 10
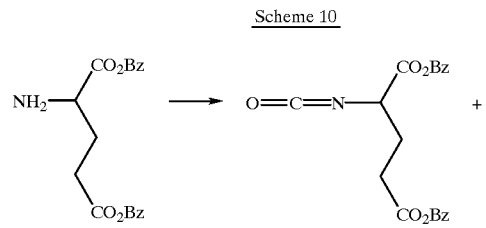
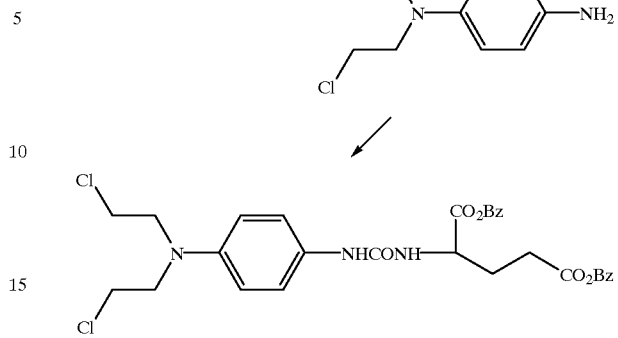
Scheme 11
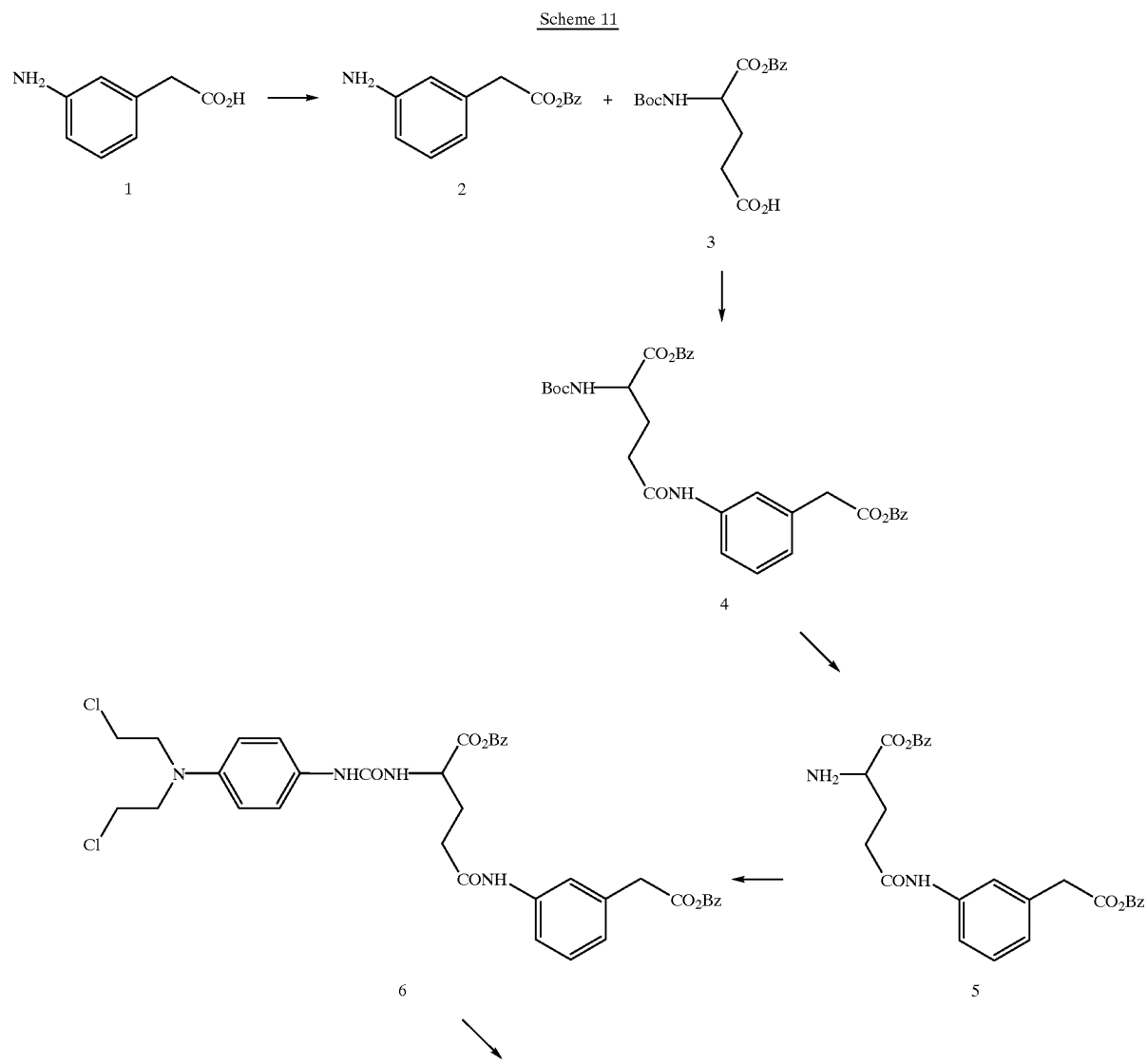

-continued

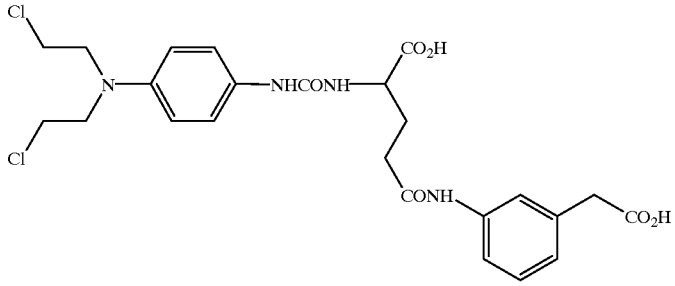

7

What is claimed is:

1. A pharmaceutical composition comprising as prodrug ingredient a compound of Formula I

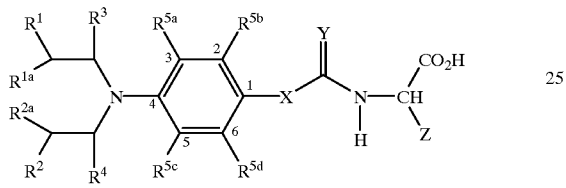

Formula I or a pharmaceutically acceptable salt of said compound, and a pharmaceutically acceptable diluent or carrier, wherein:

$R^1$ and $R^2$ each independently is I, Br, Cl, $OSO_2Me$, wherein Me is meithyl, and $OSO_2$phenyl, wherein phenyl is substituted with 1 or 2 substituents in the 2 and/or 4 positions independently selected from $C_{1-4}$alkyl, halogen, —CN or —$NO_2$;

$R^{1a}$ and $R^{2a}$ each independently is hydrogen, $C_{1-4}$alkyl or $C_{1-4}$haloalkyl;

$R^3$ and $R^4$ each independently is hydrogen, $C_{1-4}$ alkyl or $C_{1-4}$ haloalkyl;

$R^{5a}$, $R^{5b}$, $R^{5c}$ and $R^{5d}$ each independently is hydrogen, $C_{1-4}$ alkyl, optionally comprising one double bond or one triple bond, $C_{1-4}$ alkoxy, halogen, cyano, —$NH_2$, —$CONR^7R^8$, wherein $R^7$ and $R^8$ are as defined below, —NH($C_{1-4}$alkyl), —N($C_{1-4}$alkyl)$_2$ or $C_{2-5}$alkanoyl; or $R^{5a}$ and $R^{5b}$ together is a) $C_4$ alkylene, optionally having one double bond;
b) $C_3$ alkylene; or
c) —CH=CH—CH=CH—, —CH=CH—$CH_2$— or —$CH_2$—CH=CH—, each optionally substituted with 1, 2, 3 or 4 substituents, said substituents each independently selected from the group consisting of $C_{1-4}$ alkyl, $C_{1-4}$ alkoxy, halogen, cyano, nitro, $C_{2-5}$alkanoyl and —$CONR^7R^8$, wherein $R^7$ and $R^8$ are as defined below;

X is O or NH;

Y is O;

Z is —V—W where V is —$CH_2$—T— in which T is —$CH_2$—, —O—, —S—, —(SO)— or —($SO_2$)—, provided that when V has sulphur or oxygen as its second atom W is other than —COOH, and said group V optionally further carrics one or two substituents $Q^1$ and $Q^2$ on a carbon, wherein $Q^1$ and $Q^2$ each independently is $C_{1-4}$ alkyl or halogen or, when $Q^1$ and $Q^2$ are bonded to adjacent carbon atoms, $Q^1$ and $Q^2$ together optionally are a $C_3$–$C_4$alkylene radical, optionally substituted with 1, 2, 3 or 4 substituents independently selected from the group consisting of $C_{1-4}$alkyl and halogen; and W is:

(1) —COOH;

(2) —(C=O)—O—$R^6$, wherein $R^6$ is a $C_{1-6}$alkyl, $C_{3-6}$cycloalkyl or aryl group, wherein aryl is phenyl;

(3) —(C=O)—$NR^7R^8$, wherein $R^7$ and $R^8$ each independently is hydrogen or a $C_{1-6}$alkyl, $C_{3-6}$cycloalkyl, aryl, heteroaryl linked to N via a carbon atom, or $C_{7-9}$aralkyl group, wherein aryl is phenyl;

heteroaryl is a 5 or 6 membered ring containing 1 to 3 heteroatoms selected from the group consisting of nitrogen and sulphur; and the aryl moiety per se, the heteroaryl moiety and the aryl moiety of the aralkyl group are optionally substituted on carbon with 1–4 substituents selected from the group consisting of —COOH, —OH, —$NH_2$, —$CH_2$—$NH_2$, —$(CH_2)_{1-4}$-COOH, tetrazol-5-yl and —$SO_3H$, and the alkyl moiety optionally carries a methyl group;

(4) —$SO_2NHR^9$ wherein $R^9$ is as defined above for $R^7$, or, additionally, —$CF_3$, —$CH_2CF_3$ or aryl as defined above;

(5) $SO_3R^{10}$ in which $R^{10}$ is H, $C_{1-6}$alkyl or $C_{3-6}$cycloalkyl;

(6) $PO_3R^{10}R^{10}$, wherein the $R^{10}$ radicals, which are the same or different, and are as defined in 5 above;

(7) a tetrazol-5-yl group;

(8) —CONH—$SO_2R^{11}$ in which $R^{11}$ is (a) $C_{3-7}$cycloalkyl;

(b) $C_{1-6}$-alkyl, optionally substituted with one or more substituents selected from the group consisting of aryl as defined in 8c below, $C^{1-4-}$alkyl, $CF_3$ or halogen; or (c) perfluoro-$C_{1-6}$alkyl;

wherein aryl is phenyl or phenyl having 1–5 substituents, wherein the substituents are selected from the group consisting of halogen, —$NO_2$, —$CF_3$, $C_{1-4}$alkyl, $C_{1-4}$alkoxy, —$NH_2$, —$NHCOCH_3$, —$CONH_2$, —$OCH_2COOH$, —NH($C_{1-4}$alkyl), —N($C_{1-4}$alkyl)$_2$, —$NHCOOC_{1-4}$alkyl, —OH, —COOH, —CN and —$COOC_{1-4}$alkyl; or (9) —M-Het, wherein M is S, SO or $SO_2$, and Het is a 5 or 6 membered heterocyclic aromatic ring linked to M via a carbon atom of the aromatic ring, said aromatic ring containing 1, 2, 3 or 4 heteroatoms selected from the group consisting of O, N and S, said aromatic ring optionally being substituted on carbon atoms of the ring with 1, 2, 3 or 4 substituents selected from the group consisting of —OH, —SH, —CN, —CF$_3$, —NH$_2$ and halogen.

2. The pharmaceutical composition according to claim 1 wherein R$^{1a}$ and R$^{2a}$ each independently is —CH$_3$ or hydrogen.

3. The pharmaceutical composition according to claim 1 wherein R$^3$ and R$^4$ each independently is hydrogen, methyl or CF$_3$.

4. The pharmaceutical composition according to claim 1 wherein R$^{5a-d}$ each independently is hydrogen, fluorine, chlorine, methyl, —CONH$_2$ or CN.

5. The pharmaceutical composition according to claim 1 wherein R$_{5a-d}$ each independently is hydrogen.

6. The pharmaceutical composition according to claim 1 wherein V is —CH$_2$—CH$_2$—, and W is (1), (2), (3), (4), (5), (6), (8) or (9) as defined in claim 1.

7. The pharmaceutical composition according to claim 1 wherein W is selected from (1), (2), (3), (7) or (9) as defined in claim 1.

8. The pharmaceutical composition according to claim 1 wherein W represents —COOH, tetrazol-5-yl or —CONH(aryl), in which aryl is as defined in (3) of claim 1.

9. The pharmaceutical composition according to claim 1 wherein:

R$^{1a}$ and R$^{2a}$ each independently is —CH$_3$ or hydrogen;

R$^3$ and R$^4$ each independently is hydrogen, methyl or CF$_3$;

R$^{5a-d}$ each independently is hydrogen, fluorine, chlorine, methyl, —CONH$_2$ or CN;

V is —CH$_2$—CH$_2$—; and

W is (1), (2), (3), or (9) as defined in claim 1.

10. The pharmaceutical composition according to claim 9, wherein:

R$_{5a-d}$ each independently is hydrogen; and

W is —COOH, tetrazol-5-yl or —CONH(aryl), in which aryl is as defined in (3) of claim 1.

11. The pharmaceutical composition according to claim 1 wherein V is —CH$_2$—S— and W is tetrazol-5-yl.

12. The pharmaceutical composition according to claim 1 wherein:

R$^{1a}$ and R$^{2a}$ each independently is —CH$_3$ or hydrogen;

R$^3$ and R$^4$ each independently is hydrogen, methyl or CF$_3$;

R$^{5a-d}$ each independently is hydrogen, fluorine, chlorine, methyl, —CONH$_2$ or CN;

V is —CH$_2$—S—; and

W is tetrazol-5-yl.

13. A pharmaceutical composition comprising a compound selected from:

a) (S)-2(4-[N,N-bis(2-chloroethyl)amino]-phenoxycarbonylamino)-4-(1H-1,2,3,4-tetrazol-5-yl)butyric acid or a pharmaceutically acceptable salt thereof;

b) N-(4-[N,N-bis(2-chloroethyl)amino]-3-fluorophenylcarbamoyl)-L-glutamic acid or a pharmaceutically acceptable salt thereof; and c) N-(4[N,N-bis(2-chloroethyl)amino]-phenylcarbamoyl)-L-glutamic acid or a pharmaceutically acceptable salt thereof; and a pharmaceutically acceptable diluent or carrier.

14. A pharmaceutical composition comprising N-(4[N,N-bis(2-chloroethyl)amino]-phenylcarbamoyl)-L-glutamic acid or a pharmaceutically acceptable salt thereof; and a pharmaceutically acceptable diluent or carrier.

15. A pharmaceutical composition comprising N-(4[N,N-bis(2-iodoethyl)amino]-phenylcarbamoyl)-L-glutamic acid or a pharmaceutically acceptable salt thereof; and a pharmaceutically acceptable diluent or carrier.

* * * * *

UNITED STATES PATENT AND TRADEMARK OFFICE
CERTIFICATE OF CORRECTION

PATENT NO.    : 6,277,880 B1
DATED         : August 21, 2001
INVENTOR(S)   : Burke et al.

It is certified that error appears in the above-identified patent and that said Letters Patent is hereby corrected as shown below:

Title page,
Item [63], under Related U.S. Application Data, please correct Item [63] to read as follows:
-- [63] Continuation of application No. 08/956,008, filed on Oct. 22, 1997, now Pat No. 5,958,971, which is a continuation of application No. 08/722,669, filed on Sep, 30, 1996, now Pat. No. 5,714,148, which is a division of application No. 08/361,424, filed on Dec. 21, 1994, now Pat. No. 5,587,161, which is a division of application No. 08/094,952, filed on Jul. 22, 1993, now Pat. No. 5,405,990. --

Column 1,
Lines 3-9, please correct the first paragraph to read as follows:
--      This is a continuation of application Ser. No. 08/956,008, filed on Oct. 22, 1997, now Pat U.S. No. 5,958,971, which is a continuation of Ser. No. 08/722,669, filed Sep, 30, 1996, now U.S. Pat. No. 5,714,148, which is a division of U.S. Ser. No. 08/361,424, filed Dec. 21, 1994, now U.S. Pat. No. 5,587,161, which is a divisional of U.S. Ser. No. 08/094,952, filed on Jul. 22, 1993 now Pat. No. 5,405,990. --

Signed and Sealed this

Thirtieth Day of July, 2002

*Attest:*

*Attesting Officer*

JAMES E. ROGAN
*Director of the United States Patent and Trademark Office*